United States Patent [19]
Gerl et al.

[11] Patent Number: 5,811,268
[45] Date of Patent: Sep. 22, 1998

[54] MONOCLONAL ANTIBODIES FOR SELECTIVE IMMUNOLOGICAL DETERMINATION OF HIGH MOLECULAR WEIGHT, INTACT LAMININ FORMS IN BODY FLUIDS

[75] Inventors: Martin Gerl, Kriftel; Cornelia Steinert, Frankfurt am Main; Manfred Quint, Wiesbaden; Rupert Timpl, Gauting, all of Germany

[73] Assignee: Hoechst Aktiengesellschaft, Frankfurt am Main, Germany

[21] Appl. No.: 512,930

[22] Filed: Aug. 9, 1995

[30] Foreign Application Priority Data

Aug. 11, 1994 [DE] Germany ................. 44 28 481.0

[51] Int. Cl.$^6$ .................. C12N 5/00; C12N 21/04; C07K 16/00
[52] U.S. Cl. ............... 435/70.21; 435/7.1; 435/326; 530/388.1; 530/387.1; 530/350
[58] Field of Search ............. 530/387.1, 388.1, 530/350; 435/240.27, 7.1, 326, 70.21

[56] References Cited

PUBLICATIONS

Line, S.R.P. et al. 1990. Braz. J. Med. Biol. Res. 23(9):841–856 Brocks, D.G. et al 1986. In. Chem. 32(5):787–791.
Rolide, H. et al. 1979. Eur. J. Biochem. 102:195–201
Goding, J.W. ed. Monoclonal Antibodies:Principle & Practice, 1986. Academic Press, N.Y, pp. 61, 71–72, 89–90.
Timpl, R., "Structure and Biological Activity of Basement Membrane Proteins," Eur. J. Biochem. 180:487–502 (1989).
Burgeson et al., "A New Nomenclature for the Laminins," Matrix Biology 14:209–211 (1994).
Leivo et al., "Merosin, a Protein Specific for Basement Membranes of Schwann Cells, Striated Muscle, and Trophoblast, Is Expressed Late in Nerve and Muscle Development," Proc. Natl. Acad. Sci. USA 85:1544–1548 (1988).
Hunter et al., "A Laminin–Like Adhesive Protein Concentrated in the Synaptic Cleft of the Neuromuscular Junction," Nature 338:229–234 (1989).
Marinkovich et al., "The Anchoring Filament Protein Kalinin Is Synthesized and Secreted as a High Molecular Weight Precursor," J. Biol. Chem. 267(25):17900–17906 (1992).
Marinkovich et al., "The Dermal–Epidermal Junction of Human Skin Contains a Novel Laminin Variant," J. Cell. Biol. 119(3):695–703 (1992).
Kropf et al., "Logistic–Regression Model for Assessing Portal Hypertension by Measuring Hyaluronic Acid (Hyaluronan) and Laminin in Serum," Clin. Chem. 37(1):30–35 (1991).

Niemelä et al., "Type IV Collagen and Laminin–Related Antigens in Human Serum in Alcoholic Liver Disease," Eur. J. Clin. Investig. 15:132–137 (1985).
Katayama et al., "Urinary Laminin Fragments as a Tumor Marker Potentially Reflecting Basement Membrane Destruction," Br. J. Cancer 65:509–514 (1992).
Horikoshi et al., "Serum Laminin P1 Fragment Concentration in Renal Diseases," Clin. Chem. Acta. 196:185–192 (1991).
Iwata, K., "One–Step Sandwich Enzyme Immunoassay for Human Laminin Using Monoclonal Antibodies," Clin. Chem. Acta. 191:211–220 (1990).
Wewer et al., "Human Laminin Isolated in a Nearly Intact, Biologically Active Form from Placenta by Limited Proteolysis," J. Biol. Chem. 258(20):12654–12660 (1983).
Brown et al., "Protein Binding and Cell Adhesion Properties of Two Laminin Isoforms (AmB1eB2e, AmB1sB2e) From Human Placenta," J. Cell Science 107:329–338 (1994).
Harlow, et al., "Labeling Antibodies," Ch. 9 in Antibodies: A Laboratory Manual pp. 319–359 (1988).
Harlow, et al., "Immunoassays," Ch. 14 in Antibodies: A Laboratory Manual pp. 553–612 (1988).
Risteli et al., "Isolation and Characterization of Pepsin Fragments of Laminin from Human Placental and Renal Basement Membranes," Biochem. J. 193:749–755 (1981).
Engel, J., "EGF–Like Domains In Extracellular Matrix Proteins: Localized Signals for Growth and Differentiation?" FEBS Letters 251(1, 2):1–7 (1989).
Ehrig et al., "Merosin, a Tissue–Specific Basement Membrane Protein, is a Laminin–Like Protein," Proc. Natl. Acad. Sci. USA 87:3264–3268 (1990).
Chaiken et al., "Analysis of Macromolecular Interactions Using Immobilized Ligands," Analytical Biochem. 201:197–210 (1992).
Stracke et al., "Diabetische Cheiropathie—Kollagenparameter als Markersubstanzen dieser Spätkomplikation?" Die Medizinesche Welt 44:383–385 (1993).

*Primary Examiner*—Lila Feisee
*Assistant Examiner*—Minh-Tam Davis
*Attorney, Agent, or Firm*—Finnegan, Henderson, Farabow, Garrett & Dunner, L.L.P.

[57] ABSTRACT

Monoclonal antibodies directed to the laminin P1 domain for selective immunological determination of native, high molecular weight, intact laminins in body fluids; a process for preparing these antibodies; and their use for diagnosing diseases. These antibodies preferably bind to intact, native laminin, in particular to the structures of the laminin P1 domain of laminin which are folded in a native manner.

17 Claims, 9 Drawing Sheets

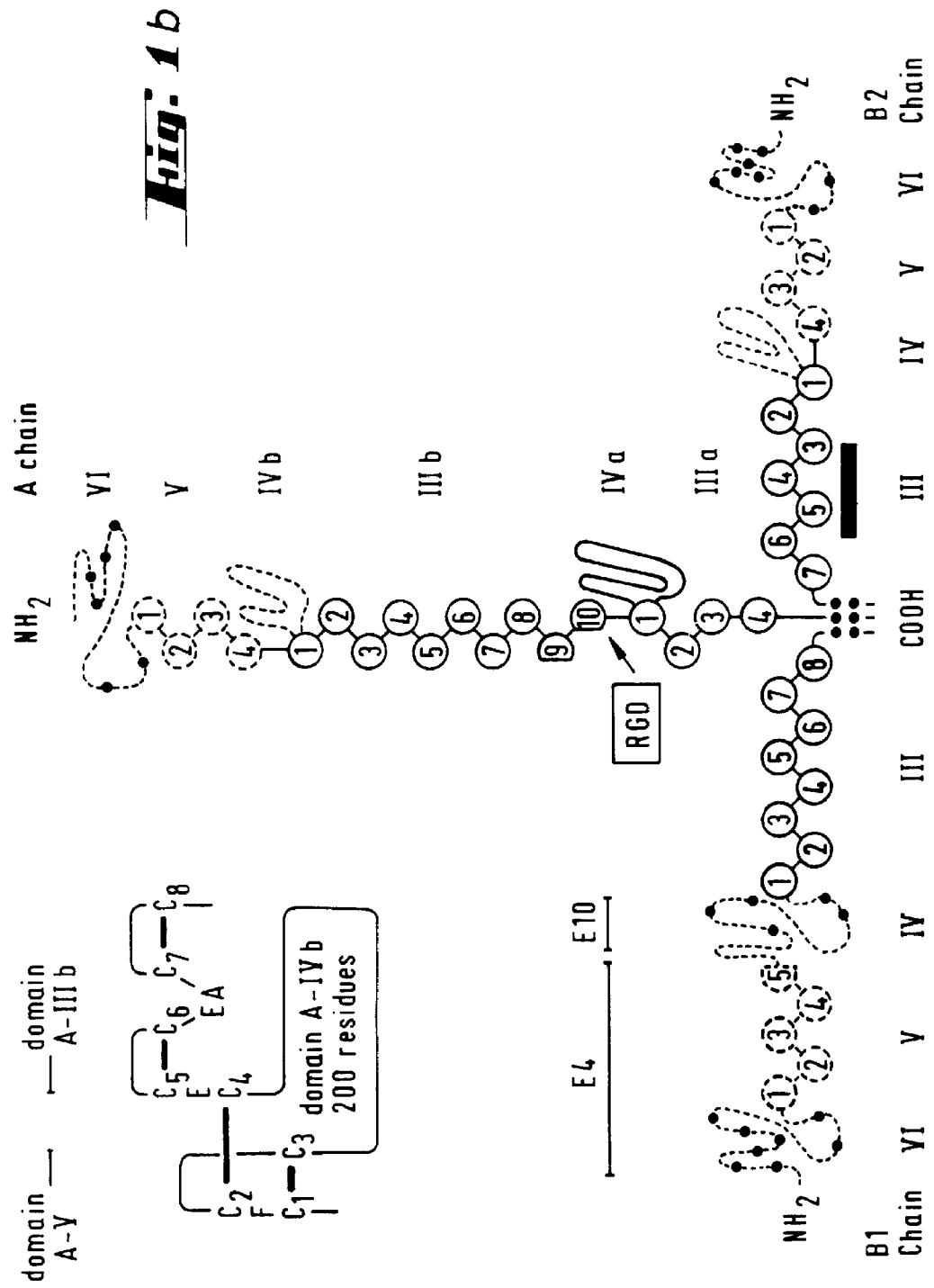

MONOCLONAL ANTIBODIES FOR SELECTIVE IMMUNOLOGICAL DETERMINATION OF HIGH MOLECULAR WEIGHT, INTACT LAMININ FORMS IN BODY FLUIDS

CLAIM OF PRIORITY UNDER 35 U.S.C. § 119

This application claims the benefit under 35 U.S.C § 119 of earlier filed foreign application, Federal Republic of Germany, P 44 28 481.0, filed Aug. 11, 1994.

The present invention relates to monoclonal antibodies for the selective immunological determination of high molecular weight laminin forms in body fluids, to a process for preparing these antibodies, and to their use for diagnosing diseases.

Laminin is a multidomain protein which is found in all basal membranes and is complexed to various other typical components of the basal membrane such as nidogen, heparan sulfate proteoglycan or collagen IV (Timpl, R. (1989) Eur. J. Biochem. 180; 487 to 502). It is composed of three different, disulfide-linked polypeptides. This gives laminin the structure of an asymmetrical cross (FIGS. 1a and 1b). Very recently, many structural variants have been identified which arise by assembling 8 (presently known) different subunits. In order to obtain an isoform of laminin, polypeptides from three different molecule classes must always be assembled together: an α chain (previously A chain), a β chain (previously B1 chain) and a γ chain (previously B2 chain) (Burgeson, R. E.; et al. (1994) Matrix Biology, Vol. 14, 209 to 211).

A large number of interesting biological functions are attributed to the laminins, such as exerting an influence on cell growth, cell spreading and axonal growth and also inducing differentiation processes (Timpl, R. (1989) Eur. J. Biochem. 180; 487 to 502).

Although laminins are typical components of all basal membranes, a distinguishing feature of different isoforms is that they have very specific tissue distributions. For example, merosin (=laminin 2; α2,β1,γ1) is a constituent of basal membranes of Schwann cells, striated muscles and trophoblasts (Leivo, I.; Engvall, E. (1988) Proc. Natl. Acad. Sci. USA 85; 1544 to 1548). Another variant, s-laminin (=laminin 3; α1,β2,γ1) can be found in the basal membrane of synapses at neuromuscular end plates, in the endothelium of blood vessels and in glomerular podocytes (Hunter, D. D.; Shah, V.; Merlie, J. P.; Sanes, J. R. (1989) Nature 338; 229 to 234). A third example, K-laminin (=laminin 6; α3,β1/β2, γ1) is specific for the basal membranes of the skin (Marinkovich, M. P.; Lunstrom, G. P.; Burgeson, R. E. (1992a) J. Biol. Chem. 267; 17900 to 17906). Kalinin/nycein (=laminin 5, α3,β3,γ2), which is typical of epithelial tissue, can also be found that this site as a component of anchoring filaments (Marinkovich, M. P.; Lunstrom, G. P.; Keene, D. R., Burgeson, R. E. (1992b) J. Cell. Biol. 119; 695 to 703).

Specific determination methods for detecting laminin in human serum have been developed for diagnosing various diseases. Possible indications which are cited are hepatic fibrosis/cirrhosis, alcoholic liver fibrosis, diabetic complications of the BM, renal diseases, chronic inflammatory arthrosis/chronic polyarthritis, and tumor diseases (Kropf. J.; et al. (1991) Clin Chem. 37; 30; Niemelä, O.; Risteli, L.; Sotaniemi, E. A.; Ristelli, J. (1985) Eur. J. Clin. Invest. 15; 132 to 137; Katayama, M.; Kamihagi, K.; Hirai, S.; Murakami, K.; Hino, F.; Kate, I. (1992) Br. J. Cancer 65; 509 to 514; Brocks, D. G.; Strecker, H.; Neubauer, H. P.; Timpl, R. (1986) Clin. Chem. 32; 787 to 791; Horikoshi, S.; Koide, H. (1991) Clin. Chim. Acta 196; 185 to 192).

Currently, three methods for determining laminin can be obtained commercially:

Method 1

A method for determining laminin P1, which is based on using a polyclonal antiserum, is marketed by Behringwerke AG under the registered trademark "RIA-gnost®" (Brocks, D. G.; Strecker, H.; Neubauer, H. P.; Timpl, R. (1986) Clin. Chem. 32; 787 to 791).

Method 2

An EIA immunoassay for laminin, which is based on using two monoclonal antibodies (TAKARA, Shuzo Co., LTD; Katayama et al., 1992; Katayama, M.; Kamihagi, K.; Hirai, S.; Murakami, K.; Hino, F.; Kate, I. (1992) Br. J. Cancer 65; 509 to 514).

Method 3

A one-step sandwich enzyme immunoassay which is based on using two monoclonal antibodies (Fuji Chemical Ltd.; Iwata, K. (1990) Clin. Chim. Acta 191; 211 to 220).

While antibodies against the pepsin-resistant fragment "Lam P1" are used in methods 1 and 3, method 2 is based on using antibodies against a "native laminin" which is isolated by the method of Wewer et al. (mild digestion with pepsin in the absence of EDTA; Wewer, U.; Albrechtsen, R.; Manthorpe, M.; Varon, S.; Engvall, E.; Rouslahti, E. (1983) J. Biol. Chem. 285; 12654 to 12660). It is evident from the work of Katayama (method 2) that the TAKARA immunoassay correlates relatively well with the RIA-gnost® (Behringwerke) method (r=0.68), although an antigen distribution which differs from that of the RIA-gnost® method is present in a (lung) tumor serum. Thus, following gel filtration chromatography, two antigenic peaks in the molecular weight range of from 330 to 150 kDa are detected in the serum by the antibodies directed against "native laminin". Owing to their size, these antigenic peaks must be degradation products of "serum laminin". In contrast to this, the RIA-gnost® method (method 1) diagnoses two peaks in the range of from 100 to 900 kDa, that is, evidently, both native (intact) and degraded structures. Nevertheless, the joint recognition of intact and degraded laminin structures leads to inaccuracies in diagnostic prediction since, on the one hand, the normal cohort and the patient cohort can overlap and, on the other hand, variations in concentration in one peak can be evened out by contrary alterations in the content of the other peak. The Fuji immunoassay (method 3) does not involve any serum chromatography. However it is evident from an SDS gel electrophoresis and an immunoblot that the antibodies which are used recognize a band at 200 kDa in normal serum and in "liver cirrhosis serum", that is evidently react specifically with degraded fragments of laminin.

In contrast, the object of the present invention is to make available monoclonal antibodies, and a process for their preparation, which preferably bind to intact, native laminin, in particular to the structures of the laminin P1 domain of laminin which are folded in the native manner.

Another underlying object of the present invention is to make available a method for the immunological determination of laminin which is based on the antibodies to be developed, which method only detects the high molecular weight population of laminin, thereby making it possible, by avoiding concomitant detection of laminin degradation products, to achieve a more accurate determination of the content of intact laminin, or of two subpopulations of laminin, in body fluids. A diagnostic method which is based on determining laminin in this manner thereby eliminates the inaccuracies in diagnostic prediction which have had to be accepted when using the previously known determination methods.

According to the invention, the object is achieved by a monoclonal antibody 1. having specificity for proteins from the family of the laminins and the laminin P1 fragment which can be prepared from human placenta by pepsin digestion, which antibody is notable for the fact that it preferably binds to the structures of the laminin P1 domain of laminin which are folded in the native manner and that its affinity for intact, native laminin is approximately equal to its affinity for the laminin P1 fragment,
2. which antibody is preferably also notable for the fact that it is formed by a hybridoma which arose by fusing cells from a myeloma cell line and lymphocytes from a vertebrate, which had previously been immunized with laminin P1, and was then purified as depicted in Tables 4 to 7 and subsequently selected, and for the fact that the antibody which is formed also exhibits, in addition to good binding affinity for purified human laminin from placenta, a good reaction with the high molecular weight form of the laminin isolated from human serum.
3. The monoclonal antibody according to the present invention also preferably exhibits the binding properties depicted in Tables 1 and 2, and
4. preferably has the ability to bind to the antigen as a pair together with an additional antibody according to the invention.

The object which is posed is furthermore achieved by a hybridoma cell line which produces an antibody having the properties listed under Nos. 1 to 4 and which can be prepared by fusing cells from a myeloma cell line and lymphocytes from a vertebrate, which has previously been immunized with laminin P1, and subsequently selecting the hybrids on the basis of whether the antibody produced by the hybrid also exhibits, in addition to good binding affinity for purified human laminin from placenta, a good reaction with the high molecular weight form of the laminin isolated from human serum.

Such a hybridoma cell line is preferably notable for the fact that the lymphocytes are removed from mice of the Balb/c strain which have been immunized with laminin P1 and the myeloma cell line is the mouse myeloma cell line P3X63AG8.653.

Three hybridoma cell lines which exhibit the abovementioned properties were deposited, on Jul. 12, 1994 under deposition numbers DSM ACC2181, DSM ACC2180 and DSM ACC2182, with the Deutsche Sammlung von Mikroorganismen und Zellkulturen GmbH (DSM) (German collection of microorganisms and cell cultures), Mascheroder Weg 1b, D-38124-Braunschweig, in accordance with the provisions of the Budapest treaty.

These hybridoma cell lines produce monoclonal antibodies which exhibit the advantageous properties listed under Nos. 1 to 4.

The hybridoma cell lines DSM ACC2181 and DSM ACC2180 in each case produce an antibody of the IgG2a subclass while the hybridoma cell line DSM ACC2182 produces an antibody of the IgG1 subclass.

In order to achieve the object which was posed at the outset, a process is also made available for preparing a monoclonal antibody according to the invention, wherein a) vertebrates are immunized with the laminin P1 fragment which can be prepared from human placenta by pepsin digestion,
b) lymphocytes are isolated from the immunized vertebrates and fused with myeloma cells,
c) the hybrids are selected with regard to the presence of an antibody having the properties given under Nos. 1 to 4 and cloned, and
d) the antibody is isolated from these clones.

This process is preferably such that the hybridoma cell lines DSM ACC2181, DSM ACC2180 or DSM ACC2182 are employed for carrying out process step d).

In addition to this, the object posed is achieved by a method for the immunological determination of native laminin using a coating antibody, which is bound adhesively or covalently to a support material, and a labeled second antibody which recognizes the antigen bound to the coating antibody, wherein the coating antibody is a monoclonal antibody in accordance with the present invention.

Preferably, however, the object posed is achieved by a method for the immunological determination of native laminin using a coating antibody, which is bound adhesively or covalently to a support material, and a labeled second antibody which recognizes the antigen bound to the coating antibody, wherein the labeled second antibody is a monoclonal antibody in accordance with the present invention.

In this context, the coating antibody can also be a monoclonal antibody in accordance with the present invention; preferably, it is that antibody which is produced by the hybridoma cell line DSM ACC2181 and which exhibits the binding constants given in Table 3. The monoclonal antibodies according to the invention can be used, in particular, in methods for diagnosing diseases which are associated with a change in the laminin content of body fluids, with the body fluids being removed from the living body but not being returned to it.

In that which follows, the invention, and in particular the preferred embodiments, are explained in detail. The invention is also defined by the patent claims.

In order to prepare the monoclonal antibodies, animals, preferably rodents, for example mice, rats, rabbits and guinea pigs, can be immunized, in the presence of adjuvant, with laminin P1 which has been isolated in accordance with the method described in Example 1.

Mice, in particular those of the Balb/c strain, are particularly preferably employed. The immune response is amplified by repeated secondary injections, for example at intervals of from 4 to 8 weeks. The success of the immunization is monitored by determining the concentration of specific antibodies using an ELISA which is known per se to the person skilled in the art. A few days before fusing the lymphocytes with a myeloma cell line, the animals are treated with laminin P1 without adjuvant. Lymphocytes are isolated from the animals and fused with a myeloma cell line which can also derive from one of the abovementioned animal species, preferably, however, the mouse, in particular with cell line P3X63AG8.653. Advantageously, lymphocytes are fused with myeloma cell lines from the same species. The fusion, and subsequent cultivation of the cell clones, are carried out in a manner known to the person skilled in the art with the concentration of specific antibodies in the supernatant of the cell culture being determined by means of immunological binding tests. Cell clones which are suitable for use in immunological methods are selected from the clones arising from the fusion using a screening sequence depicted in Tables 4 and 5. Particularly preferably, cell lines are used which are prepared by fusing anti-laminin P1 lymphocytes from mice of the Balb/c strain with the mouse myeloma cell line P3X63AG8.653.

The monoclonal antibodies according to the invention belong to the group of the immunoglobulins, preferably to the IgG, IgA and IgM protein classes. Antibodies of the IgG2a and IgG1 subclasses may particularly advantageously be employed. The antibody according to the invention is notable, in particular, for the fact that its affinity for intact laminin is approximately equal to its affinity for the immunizing antigen laminin P1, which is produced by pepsin digestion (Tables 2 and 3). The screening strategy depicted in Tables 4 and 5 clearly shows that the overwhelming majority of the clones isolated from the fusion in fact produce monoclonal antibodies which only recognize the artificial laminin P1 fragment which is produced by pepsin treatment. It is highly probable that these antibodies react with immunogenic structures which were artificially produced as a result of proteolytic chain cleavage and which are not present in the native structure of the protein. Only a few of the monoclonal antibodies which were isolated, in particular, however, the antibodies according to the present invention, react with the native structures, which were not generated by pepsin digestion, in the central domain of the laminin.

It is important for preparing and characterizing the antibodies according to the invention that a suitable source is available for isolating both the immunizing antigen and the different structural variants which are crucial for the screening. Human laminin P1 and various laminin preparations are purified from human placenta using the methods described in the examples. At least two different laminin isoforms can be obtained from this organ (Brown, C. J.; Wiedemann, H.; Timpl, R. (1994) J. Cell Sci. 107; 329 to 338).

The antibodies according to the invention can be used in various immunological methods, such as immunoradiometric tests after labeling the tracer antibody with chloramine T or Bolton-Hunter reagent, and also other competitive and non-competitive binding assays such as fluorescence immunoassays, enzyme immunoassays, chemiluminescence immunoassays or other types of immunoassay, including all forms of radioimmunoassay (Harlow, E.; Lane, D. (1988) Antibodies: A Laboratory Manual, CSH; 2nd Edn.; New York; 319 to 359; 553 to 612). In this context, it does not matter whether the coating antibody is covalently or non-covalently bound to polystyrene tubes, polystyrene beads, paramagnetic particles or activated column materials of any kind. For this reason, the monoclonal antibodies can be employed in immunological methods for the isolation and characterization, and also for the quantitative determination, of laminin in tissues and body fluids. Methods are followed which are known per se to the person skilled in the art, with a liquid sample which contains laminin being reacted with one of the monoclonal antibodies according to the invention, which is either in solution or preferably bound to a solid support, and the quantity of the laminin being determined by way of the antigen/antibody complex which is formed. These immuno-assays do not recognize laminin degradation products in body fluids, which degradation products were either detected concomitantly or recognized exclusively in previous immunological determinations, and only recognize intact laminin structures.

The invention is explained in more detail in the following examples.

EXAMPLE 1

Preparation of Human Laminin P1 (Immunizing Antigen)

The immunizing antigen laminin P1 is a laminin fragment of from 200 to 250 kDa in size which can be extracted and isolated following intensive digestion of placenta tissue with pepsin. This fragment contains the inner, rod-shaped domains (III domains) of the short arms of the α, β and γ laminin chains (Risteli, L; Timpl, R. (1981) Biochem. J. 193, 749 to 755). The three polypeptide chains (of which several isoforms exist) are linked by disulfide bridges and are characterized by an identical three-dimensional structure. As depicted in FIG. 1b, from seven to fourteen structural motifs, so-called EGF-like repeats, which are strung together linearly and which are all characterized by the same folding pattern, are present in the individual chain segments of the laminin subunits. The 50 to 60 amino acids which are present in each of the EGF-like repeats assume a cloverleaf-shaped structure as the result of a typical, predetermined sequence of disulfide bonds. At the sequence level, there is an identity of >30% between the EGF-like repeats of the short laminin chains (Engel, J. (1989) FEBS Lett. 251, No. 1.2; 1 to 7).

The immunizing antigen laminin P1 was prepared as explained below:

1. Thawing 1.2 kg of human placenta were thawed, at 4° C. for from 16 to 20 hours, in 500 ml of water+PI.

(PI=protease inhibitors=1 mM NEM, 1 mm PMSF and 0.28 mM PCMB).

2. Homogenization

Following thawing, the volume of the sample was adjusted to 2.5 l and the sample was homogenized with an Ultra-turrax for from 3 to 5 minutes.

The sample was finally centrifuged at 6500×g for 10 minutes at 4° C.

3. Washing

The sediment which was obtained was stirred up 8 times with 1.8 l of 3M NaCl, 0.1% Triton X-100, 0.02M Tris/HCl, pH 7.4+PI on each occasion and then centrifuged at 6500×g for 10 minutes at 4° C. Finally, the sediment was stirred in water and centrifuged once again. The sediment was then extracted, at 4° C. for 64 hours, with 3 l of buffer (1M NaCl, 10 mM EDTA, 1% Triton X-100, 0.02M Tris/HCl, pH 8.6+PI). Insoluble material was separated off by centrifuging at 26000×g (30 minutes) and subjected to further processing.

4. Digestion with pepsin

The final sediment was stirred up in 3.0 l of 0.5M acetic acid, 10 mM EDTA, then homogenized with an Ultra-turrax for 3 minutes and stirred for a further 2 hours. The pH of the sample was then adjusted to 2.5 with formic acid. The proteolytic digestion was carried out by adding 100 mg of pepsin at 4° C. and lasted for 40 h. The turbidity which was present following the pepsin digestion was removed by centrifuging at 26000×g for 30 minutes (4° C.).

5. Acidic NaCl precipitation 366.1 g of NaCl were introduced (=1.9M), while stirring, into the centrifugation supernatant (3.16 l), which was then stirred for a further 2 hours.

The precipitate which formed was separated off from the acidic buffer by centrifuging at 6500×g (4° C., 10 min), dissolved in 1.8 L of 0.02M NaCl, 2M urea, 0.05M Tris/HCl, pH 8.6, and then dialyzed 7x against 8 L of the same buffer. Turbidity in the solution was removed by centrifugation (26000×g, 30 minutes, 4° C.).

6. Chromatography on Q Sepharose FF (5×15 cm)

5 separations were carried out with 350 ml of sample being loaded onto the column on each occasion.

Run conditions: Buffer A; 0.02M NaCl, 0.05M Tris/HCl, 1 mM EDTA pH 7.4,

Buffer B; 1M NaCl, 0.05M Tris/HCl, 1 mM EDTA, pH 7.4, flow rate; 3 ml/min linear gradient; (90 ml) of 0.02 to 0.1M NaCl
stepwise gradient; 300 ml of buffer containing 0.1M NaCl,
450 ml of buffer containing 0.25M NaCl,
300 ml of buffer containing 0.5M NaCl.

The individual chromatographic fractions were analyzed using the RIA-gnost® laminin P1 test, and the fractions containing laminin P1 (eluted at 0.25M NaCl) were pooled.

7. Ammonium sulfate precipitation

The pool containing laminin P1 was diluted 3:1 with 3M $(NH_4)_2SO_4$ and incubated at 4° C. for 2 hours. The precipitate was recovered by centrifuging at 26000×g (4° C.) for 30 minutes.

8. Chromatography on Superose 6 prep. grade 16/50

The precipitated protein was dissolved in a suitable volume of 50 mM Na phosphate, 0.15M NaCl, 0.02% Na azide, pH 2.0, and fractionated, in 2 ml portions, by gel filtration chromatography.

Run conditions: Buffer; 50 mM Na phosphate, 0.15M NaCl, 0.02% Na azide, pH 2.0, flow rate; 1.0 ml/min The individual chromatographic fractions were once again analyzed using RIA-gnost® laminin P1. The laminin-containing fractions from the 25 separate chromatographic runs were combined and treated with 2M NaOH in order to adjust the pH to 8.0. The solution was then treated 3:1 with a 3M solution of $(NH_4)_2SO_4$ and incubated overnight. The precipitate which formed was centrifuged off at 26000×g (30 minutes, 4° C.) and dissolved in 20 ml of 0.2M $NH_4HCO_3$.

9. Digestion with collagenase

Approximately 1 mg of collagenase, and also 1 spatula tip of $MgCl_2$ and $CaCl_2$, were added to the solution, which was incubated at 37° C. for 4 hours. The proteolytic digestion was stopped by adding 3 ml of formic acid.

10. Chromatography on Superose 6 prep. grade 16/50

Following the digestion, chromatography was carried out once again as described above. The fractions which were positive in the RIA were (after having been adjusted to a pH of 8.0 with 2M NaOH) diluted 3:1 with 3M $(NH_4)_2SO_4$, and stored in this form at 4° C.

The precipitate which formed was suspended in 3M $(NH_4)_2SO_4$, and this suspension was then divided into 22 portions of 0.5 ml each which were centrifuged for 4 minutes in an Eppendorf centrifuge. 0.48 ml of supernatant was removed from each of the aliquots. The isolated laminin P1 can be stored as an ammonium sulfate precipitate at 4° C. for at least 4 months without loss of content.

11. Yield/quality

Determination of concentration using the RIA-gnost® laminin P1 test: 108,600 E (23.9 mg)
Characteristics in the RIA:
linear inhibition curve
So binding=66.9%
50% intercept=1.302 E/ml
Normal serum=1.72 E/ml

EXAMPLE 2

Preparation of Laminin, Batch I

The washing steps and the extraction are carried out as described in Example 1.

The extracted protein is rebuffered in 2M urea, 0.05M Tris/HCl, 0.02M NaCl, 2 mM EDTA, pH 7.4, using an Ultrasette (300 kDa) and loaded onto a Q Sepharose FF 60/14 column. The bound protein can be eluted using 0.15M NaCl dissolved in loading buffer. The eluate is concentrated once again using the Ultrasette (300 kDa) and chromatographed on Superose 6 prep. grade 16/50 in PBS, 2 mM EDTA at a flow rate of 1 ml/min. The fractions containing laminin (determined by RIA-gnost® laminin P1) are combined, concentrated using the Ultrasette, and incubated with 5000 units of benzonase (purity II) at RT for >2 h. The sample is then loaded onto a ConA-Sepharose 4B column (2.6×10 cm) which is equilibrated with 0.15M NaCl, 0.05M Tris/HCl, pH 7.4.

The laminin can then be eluted once again, at a flow rate of 1 ml/min, using 0.4M methyl α-D-mannopyranoside in the equilibration buffer. For further purification, and for the purpose of transfer into a PBS+2 mM EDTA buffer, the eluate is chromatographed, at 1 ml/min, on a Sephacryl S500 Superfine column (2.6×140 cm).

EXAMPLE 3

Preparation of Laminin, Batch II

The washing steps and the extraction are carried out as described in Example 1.

The laminin-containing EDTA extract is concentrated down to 25 ml using an Ultrasette (300 kDa) and at the same time rebuffered into 50 mM Tris/HCl, 1 mM $MgCl_2$, pH 8.0. This solution is then incubated at room temperature for 2 hours with 5000 units of benzonase. The solution which has been treated in this way is then passed through an anti-P1 Mab affinity column to which 4 different monoclonal antibodies having binding affinities both for laminin P1 and also for intact laminin have been coupled covalently (in accordance with the manufacturer's instructions). The following monoclonal antibodies, which were designated by us in this way in order to distinguish them, were immobilized on an activated CNBr-Sepharose 4B (6 ml) column: A24/2/2 (2.7 mg), A27/2/1 (1.5 mg), A9/2/1 (0.6 mg) and A28/1/1 (5.2 mg).

25 ml of the EDTA extract, at a flow rate of 1 ml/min, are loaded onto the affinity column (equilibrated in 0.1M NaCl, 0.05M Tris/HCl, 10 mM EDTA, 0.1M Pefabloc, pH 7.4), and then eluted using 0.1M glycine/HCl, pH 2.7. The pH of the eluate must immediately be brought to neutrality using a 0.8M solution of Tris, with rebuffering into 0.1M $NH_4HCO_3$+2 mM EDTA finally taking place using a Macrosep 100 kDa.

EXAMPLE 4

Hybridoma Production

Mice of the Balb/c strain are immunized subcutaneously, in the presence of complete Freund's adjuvant, with 20 μg of laminin P1 which was obtained in accordance with Example 1. The immune reaction is amplified by a further subcutaneous injection of 20 μg of laminin P1 in the presence of incomplete Freund's adjuvant after 4 weeks and after three months. Three days prior to the fusion, the immune response is amplified by injecting a further 100 μg of laminin P1 intraperitoneally.

For the fusion, the animals are sacrificed and the spleen cells are isolated. The spleen cells are fused with the myeloma cell line P3X63AG8.653 in the presence of polyethylene glycol. Spleen cell×P3X63AG8.653 hybrids are selected by culturing the fusion mixture in hypoxanthine/aminopterin/thymidine medium for a period of two weeks. The cell clones which are obtained are subcloned repeatedly in order to achieve a stable cell line. The resulting cell colonies are tested for antibody production in various immunological binding tests. The resulting cell lines from which the antibodies designated by us for the purposes of distinction as A27/2/1, A9/2/1 and A33/2/20 are obtained were deposited on Jul. 12, 1994, under the deposition numbers DSM ACC2181, DSM ACC2180 and DSM ACC2182, with the Deutsche Sammlung von Mikroorganismen men und Zellkulturen GmbH (DSM) (German collection of microorganisms and cell cultures), Mascheroder Weg 1b, D-38124 Braunschweig, in accordance with the provisions of the Budapest Treaty.

EXAMPLE 5

Experiments directed towards characterizing and identifying specific monoclonal antibodies.

The chronological sequence of the screening is shown in Tables 4 and 5.

Immunizing mice with laminin P1 results in an extraordinarily large number of antibody-producing hybridoma clones. Consequently, a differential screening, in which the binding of the monoclonal antibodies to native or natural structures can be detected using the widest possible variety of immunological methods of analysis, had to be carried out in order to find clones which produce monoclonal antibodies against structural motifs which are present in the appropriate domain of the native laminin molecule. Antibodies which only react with purified laminin P1 were rejected immediately. In order to carry out the experiments, native laminin has to be obtained by extraction from human placenta (see Examples 2 and 3). In this regard, however, care must be taken to ensure that the spectrum of laminin isoforms which may possibly be present is not restricted to too great an extent by too extensive purification of a dominant form of laminin. It is evident from a study by Brown et al. (Brown, C. J.; Wiedemann, H.; Timpl, R. (1994) J. Cell Sci. 107; 329 to 338) that at least two different laminin variants (laminin 2 and laminin 4) can be obtained from placenta. It appeared, even in early phases of the screening process, to be of the utmost importance to test the reaction of the monoclonal antibodies with the laminin structures present in serum. For these investigations, serum laminin has to be isolated, using a Sephadex S-400 column (1.0×30 cm), from approximately 20 ml of serum derived from a healthy test subject. The serum antigens elute from the column in two broad peaks with peak 1 containing antigenic structures having molecular weights >600 kDa. Peak 2 contains degradation products of serum laminin, having molecular weights in the order of size of the immunizing antigen (approximately 200 kDa), and also smaller fragments. In the course of the screening, only those antibodies (clones) are selected which, in addition to their binding affinity for purified human placental laminin, also exhibit a good reaction with "serum laminin", preferably with the high molecular weight form of this laminin. The ability to bind to the antigen as a pair together with a second monoclonal antibody represents an additional criterion for selection. Table 6 demonstrates, using some monoclonal antibodies derived from the same immunization as an example, how the individual "screening modules" (see Tables 4 and 5) render it possible, taken overall, to characterize and select the monoclonal antibodies according to the invention. Table 7 summarizes investigations which were directed towards analyzing the binding affinities for serum laminin as compared with standard recognition.

EXAMPLE 6

Radioactive labeling of the monoclonal antibodies A27/2/1 and A9/2/1

0.2 ml of a solution containing 40 µg of the monoclonal antibodies in 0.05M phosphate buffer, pH 7.4, is initially introduced into a polystyrene test tube (12×55 mm), and 100 MBq of a solution of Na $^{125}$I, buffered with 0.5M phosphate buffer, pH 7.4, are added. After 50 µl of an aqueous solution of 20 µg of chloramine T have been added, the sample is mixed for 1 min. The iodination reaction is then terminated by adding 50 µl of an aqueous solution of 20 µg of sodium disulfite.

The unreacted Na $^{125}$I is then separated from the $^{125}$I-labeled monoclonal antibodies by chromatography on an anion exchange resin or by gel filtration chromatography on PD-10. The purified, $^{125}$I-labeled antibodies have a specific activity of from 5 to 12 mCi/mg (from 180 to 450 MBq/mg).

EXAMPLE 7

Coating Test Tubes with Antibody

In order to bind the monoclonal antibody A27/2/1 to polystyrene test tubes (12×75 mm), 0.5 ml of the monoclonal antibody A27/2/1 is incubated, at RT for 20 hours, in each tube at a concentration of 20 µg/ml in PBS. After the antibody solution has been sucked off, the tubes are blocked with 1 ml PBS/1% BSA at RT for 1 hour. After the solution has been sucked off, the tubes can be stored in a refrigerator.

EXAMPLE 8

Immunoradiometric Tests

Assay variant 1: A27/2/1–$^{125}$I A9/2/1

50 µl of sample or 100 µl of standard are pipetted into each of the coated tubes, at from 17° to 25° C., after which the tubes are filled with 150 µl of PBS/Tween. After incubating the tubes for 2 hours, the liquid is sucked off and the tubes are washed 2x. 200 µl of $^{125}$I A9/2/1 are then added and the tubes are incubated once again at RT for 2 hours. Once the liquid has been sucked off and two washings have been carried out, the bound activity can be determined in a γ counter.

Assay variant 2: A27/2/1–$^{125}$I A33/2/20

200 µl of sample or standard are pipetted into each of the coated tubes at from 17° to 25° C. 200 µl of tracer are then added and the tubes are incubated at RT for 4 hours. Once the liquid has been sucked off and two washings have been carried out, the bound activity can be determined in a γ counter.

standard antigen

Laminin P1 from the RIA-gnost® Lam-P1 kit (Behringwerke AG, Marburg) is used as the standard. In this way, the two assays have a common reference quantity and can be compared readily with each other and with the RIA-gnost® Lam-P1 test.

EXAMPLE 9

Determination of the molecular weight distribution of the standard samples and antigens, in normal sera and in pathological sera, which react in the test methods described.

Laminin P1, human laminin (batch II) and also various sera are fractionated by molecular weight using a Sepharose S-400 column. The size distribution of the laminin antigenicity is then investigated using the immunoradiometric test methods. The results obtained from a pool of normal serum are compared with the RIA-gnost® Lam P1 test. The chromatograms obtained for the standards and for a normal serum pool are shown in FIGS. 2 to 4.

Column dimensions: 1.0×30 cm

Elution buffer: PBS+0.04% Tween 20+0.02% Na azide

Flow rate: 0.2 ml/min

The column was calibrated using the molecular weight markers thyroglobulin (670 kDa), immunoglobulin (156 kDa), ovalbumin (44 kDa) and myoglobin (17 kDa).

Individual sera from patients suffering from alcoholic liver disease, PBC and CAH are depicted in FIGS. 5 to 7.

FIG. 8 shows a semidry blot attained by the standard protocol using a discontinuous buffer system after separating approximately 1 μg of laminin batch II (Example 3) by SDS gel electrophoresis (Novex ready-to-use gel containing from 4 to 12% polyacrylamide) under reducing (+SH) and non-reducing (−SH) conditions. The nitrocellulose membrane was cut into strips and the individual strips were incubated with the monoclonal antibodies A9/2/1, A27/2/1 and A33/2/20. Anti-mouse alk. phosphatase (Sigma A 5153) was used as the second antibody.

It is evident that typical, and in each case characteristic, antigen distribution patterns are recorded using the assays according to the invention. This is a clear indication that the two immunological determination methods specifically recognize different forms of laminin.

In addition to this, it can be seen that the monoclonal antibodies do not show any reaction with the denatured structures produced by reduction. Consequently, the monoclonal antibodies according to the present invention recognize structural motifs of the laminin P1 domain which are specifically folded in a native manner.

EXAMPLE 10

Determination of the binding affinities for different laminin/laminin P1 preparations Various laminin preparations were examined in order to obtain a preliminary assessment of which laminin structures are recognized by the two assays. While the following table does not permit any unambiguous assignments, it does clearly show that the two tests bind particular variants with differing priorities (affinities).

The data indicated are not able to settle the question of which isoforms of laminin are recognized by the described test methods. It would only be possible to solve this problem if several purified isoforms were available in their native form.

| Concentration determination in %, based on the total protein concentration in the sample | A27/A9 | A27/A33 |
|---|---|---|
| Laminin (Chemicon; Wewer 1983)*); | 2.7 | 1.4 |
| Merosin (Chemicon; Ehrig 1990)**); | 35.8 | 13.3 |
| Human laminin, purification see Example 2 | 21.4 | 2.8 |
| Human laminin, purification see Example 3 | 59.8 | 80.4 |
| Lam-P1: RIA-gnost ® Standard 7; % binding based on the counts employed | 64.9% | 35.4% |

*)Wewer, U.; Albrechtsen, R.; Manthorpe, M.; Varon, S.; Engvall, E.; Ruoslahti, E. (1983) J. Biol. Chem. 258; 12654 to 12600)
**)Ehrig, K.; Leivo, I.; Argraves, S.W.; Ruoslahti, E.; Engvall, E. (1990); Proc. Natl. Acad. Sci. USA 87; 3264 to 3268)

EXAMPLE 11

Cross Reactions

Table 8 shows that no significant cross reactions with selected human connective tissue and serum proteins can be detected using the two novel laminin assays. Likewise no cross reaction can be observed with laminin/nidogen and laminin P1 from the mouse EHS tumor.

EXAMPLE 12

Determination of the average serum contents in patient cohorts having different diseases Different serum cohorts were analyzed using the immunoradiometric assays according to the invention in accordance with Example 8. The results of the content determinations are summarized in Tables 9 to 17. Both test variants diagnose elevated laminin levels in the indications alcoholic liver diseases, PBC, CAH, post hepatic liver cirrhosis, decompensated liver cirrhosis, liver cirrhosis of unknown origin, and in tumor sera; laminin contents which are clearly decreased are found in the indication diabetes. On the basis of the correlations between the assays according to the invention and the RIA-gnost® laminin P1 test which are evident from the tables, it is clear that the two immunological methods differ from each other and that the two assays differ in their diagnosis from the RIA-gnost® test. This confirms the effect described in Example 9, i.e. a difference in the antigen distribution pattern.

Abbreviations
EDTA: ethylenediaminetetraacetic acid
NEM: N-ethylmaleiimide
PBS: phosphate-buffered saline (buffer solution PM 16, Serva)
PCMB: 4-hydroxymercuribenzoic acid sodium salt
PMSF: phenylmethylsulfonyl fluoride
Chemicals, enzymes
Collagenase, Worthington (CLSPA)
Pepsin, Boehringer Mannheim (No. 108057)
Benzonase, Merck Darmstadt (No. 1654)

All the chemicals employed were specified "p.A."; they were obtained from Riedel d. H. and from Merck.
Separation media
Q Sepharose® FF, Pharmacia
Superose® 6 (16/50), Pharmacia
Ultrasette® (300 kDa), Filtron
BrCN-activated Sepharose®, Pharmacia
ConA-Sepharose® 4B, Pharmacia
Sephadex® S-400, Pharmacia Explanation of Tables 1 to 3
BIAcore investigations Biospecific interactions can be followed on-line using the BIAcore® system from Pharmacia Biosensor. The principle of the measurement is based on an optical phenomenon (surface plasmon resonance), which is affected by the mass which is bound on a gold film. Expressed simply, this system involves miniaturized affinity chromatography on a gold sensor surface. The quantity of a specifically bound ligand can be depicted pictorially in the form of a resonance signal (Chaiken, I.; Rosé, S.; Karlsson, R. (1992) Anal. Biochem. 201; 197 to 210); Karlsson, R.; Altschuh, D.; van Regenmortel, M. H. V. (1992) Measurement of antibody affinity, in: Structure of Antigens; CRC Press (van Regenmortel, ed); Boca Raton, Fla.; 127 to 148).

1. Direct screening on immobilized laminin P1

Laminin P1 was immobilized on the sensor chip, at a concentration of 200 μg/ml in 10 mM Na acetate, pH=4.0, in accordance with the instructions in the user manual. A double pulse of 4 μl of 100 mM HCl can be effected in order to regenerate the Lam P1 affinity matrix. The layer of laminin P1 is extremely stable and can be used for approximately 2 months (>300 individual analyses) without any loss of quality.

In order to screen for potent antibodies, from 4 to 25 μl of culture supernatant from the individual cell colonies were passed directly over the affinity matrix; after 1 to 5 minutes, binding (relative strength) can be detected from the RU and the constancy of the signal. This makes it possible to select interesting clones in a rapid and, at the same time, meaningful manner. Successive injections of different culture supernatants without any intervening regeneration make it possible to screen for antibodies which can bind at the same time to different epitopes of the antigen.

2. Subclass determination

As described above, hybridoma supernatants were passed over the Lam P1 layer of the BIAcore® chip. Once the antibody had bound (the sample had passed through), 4 µl volumes of subclass-specific anti-mouse antibodies were then injected sequentially. Mutual binding was once again expressed by an increase in the signal. This makes it possible to assign the subclass unambiguously within 5 minutes.

3. Concentration determination

In order to achieve selective and reversible binding of mouse antibodies, a special antibody (rabbit anti-mouse Fc-specific; RAM-Fc) can be immobilized on the sensor chip of the BIAcore® by means of a standard method. Since the measuring system signal depends directly on the mass of the bound ligand, it is possible to carry out concentration determinations, in particular when the standard material and the sample to be analyzed have the same molecular weights. It is even possible to determine the concentration of a specific protein in complex mixtures since, as in the present example, the specificity of the binding only retains the mass of the desired ligand on the sensor chip.

A standard curve for determining the quantity of antibody present in the culture supernatants (=synthetic capacity of the clone) was constructed using a well-characterized monoclonal antibody (Mab 238) which was available in the laboratory. The signals of unknown samples (culture supernatants), averaged from duplicate determinations, can be converted into concentrations (µg/ml monoclonal antibody) using the standard curve. When executing such complex and time-consuming serial measurements, the BIAcore system makes use of a randomization program so that those sources of error are negated which might result from wear and tear on the affinity matrix or from differences in operating life.

4. Screening for binding affinities for human laminin

Because the human laminin in the preparation (laminin batch I) was only slightly enriched, it was not possible to immobilize it directly (as, for example, in the case of Lam P1). It was necessary, therefore, to construct an affinity matrix which was able to fish the laminin out of the heterogeneous solution. Specific antibodies from the culture supernatants were bound to the immobilized RAM-Fc (see above), thereby producing (non-covalent) affinity matrices for human laminin. The laminin sample was then passed over these specific layers. A further increase in the signal was observed when recognition took place.

5. Determination of binding constants

Using the BIAcore® system, it is possible to determine the binding of ligands quantitatively (Chaiken, I.; Rosé, S.; Karlsson, R. (1992) Anal. Biochem. 201; 197 to 201; Karlsson, R.; Altschuh, D.; van Regenmortel, M. H. V. (1992) Measurement of antibody affinity, in: Structure of Antigens; CRC Press (van Regenmortel, ed); Boca Raton, Fla.; 127 to 148), since the association phase, establishment of the binding equilibrium and the dissociation phase can be presented as chronologically separate processes. The software of the apparatus allows the measurement data to be converted relatively simply into the corresponding tabular calculations.

In order to determine the binding constants, a specific antibody (prior purification is not absolutely necessary!) must, for example, be passed over the affinity matrix in several dilutions. During the association phase, the program determines, at user-defined intervals, the RU values and the actual slope of the curve so that it is possible to plot slope/R. The association constant $K_{ass}$ can be determined if the slopes of this function for all the concentrations analyzed are related to the actual concentrations (in nM) which are present. At the highest antibody concentration, the dissociation phase of the experiment is extremely prolonged. The dissociation constant $K_{diss}$ can be determined from the plot of lnR1/Rn against time. The equilibrium constant KD is obtained from the formula $K_{ass}/K_{diss}$.

TABLE 1

| Subclass | | Human laminin binding (BIAcore) | Serum laminin Peak 1 (high molecular weight) binding | Serum laminin Peak 2 (low molecular weight) binding |
|---|---|---|---|---|
| A27/2/1 | IgG 2a | 534 RU | 19.5 µg/ml[1] | 9.6 µg/ml[1] |
| A9/2/1 | IgG 2a | 601 RU | 20.5 µg/ml[2] | 2.4 µg/ml[2] |
| A33/2/20 | IgG 1 | 154 RU | 12.3 µg/ml[2] | 1.9 µg/ml[2] |

[1] IRMA method using RIA-Ar (= polyclonal rabbit IgG; basis of the RIAgnost ® test) as the coating antibody and iodinated A27/2/1.
[2] IRMA method using A27/2/1 as the coating antibody and iodinated A9/2/1 or A33/2/20.

TABLE 2

Physical properties - binding constants

| | A27/2/1 | A9/2/1 | A33/2/20 |
|---|---|---|---|
| A) Binding constants on a Lam P1 affinity matrix | | | |
| $k_{ass}$ (1/Ms) | 2.972 × 10⁵ | 2.303 × 10⁵ | 1.72 × 10⁵ |
| $k_{diss}$ (1/s) | 6.71 × 10⁻⁶ | 8.699 × 10⁻⁶ | 1.28 × 10⁻⁶ |
| KD (1/M) | 4.43 × 10¹⁰ | 2.65 × 10¹⁰ | 1.35 × 10¹⁰ |
| B) Binding constants on a human laminin affinity matrix | | | |
| $k_{ass}$ (1/Ms) | 1.25 × 10⁵ | 4.54 × 10⁵ | 4.74 × 10⁴ |
| $k_{diss}$ (1/s) | cannot be measured in 30 min! | | |
| KD (1/M) | — | — | — |

TABLE 3

Physical properties - binding constants
Binding constants on a Mab A27/2/1 affinity matrix

| | Lam P1 | Laminin* | Laminin** |
|---|---|---|---|
| $k_{ass}$ (1/Ms) | 8.64 × 10³ | 1.14 × 10⁵ | 1.20 × 10⁵ |
| $k_{diss}$ (1/s) | 2.24 × 10⁻⁴ | 1.52 × 10⁻⁴ | 1.17 × 10⁻⁴ |
| KD (1/M) | 3.85 × 10⁷ | 7.49 × 10⁸ | 1.03 × 10⁹ |

*Human laminin purified as described under methods
**Human laminin purified by affinity chromatography on a cocktail of monoclonal antibodies The three tables show that the three monoclonal antibodies possess very good binding properties and that the antibodies are particularly notable for the fact that they bind very firmly to the immobilized antigen. For example, when the laminin layer is used, none of the antibodies is observed to dissociate during the period of analysis (30 min). Nevertheless, if dissolved antigen is passed over an A27/2/1 layer, for example, the association takes place with the same rapid kinetics ($k_{ass}$ 1.2×10⁵/Ms). However, there then follows a clear dissociation phase so that an equilibrium constant of approximately 1×10⁹ can be determined for the laminin binding.

Interestingly, the constants for binding to LamP1 differ by a factor of 1,000 depending on whether the LamP1 is immobilized (high local concentration) or whether it has to be bound from the solution. This effect could be the basis for the exclusive recognition of the high molecular weight peak (intact serum laminin) in human serum (see below).

TABLE 4

Screening strategy for monoclonal anti-LamP1/laminin antibodies

| Screening steps | Test method/Selection criterion | Selection |
|---|---|---|
| Immunization Fusion → hybridomas | Titer determination Screening with ELISA for LamP1 SELECTION CRITERIA: Recognition of LamP1 in the ELISA (magnitude of the OD) Growth of the clones in cell culture | 150 pos. clones |
| 1st Selection Culture in 24-well culture dishes | Screening with ELISA for LamP1 and for laminin-enriched extract from human placenta SELECTION CRITERIA: Strong binding to LamP1 and/or positive reaction to laminin | 56 pos. clones |
| 2nd Selection First biochemical characterization | Subclass determination using BIAcore (exclusion of IgM) screening buy SDS gel electrophoresis, Western Blot and immune staining SELECTION CRITERIA: Reaction with unreduced and/or reduced laminin | 18 pos. clones |
| Isolation of the positive clones (approximately 10–20 subcolonies per clone) Second biochem. characterization | Subclass determination using BIAcore (exclusion of IgM) screening by SDS gel electrophoresis, Western Blot and immune staining SELECTION CRITERIA: Reaction with unreduced and/or reduced laminin | |
| 3rd Selection Characterization using BIAcore | Examination of LamP1 binding (rel. strength) Examination of laminin binding (rel. strength) Subclass determination (type uniformity of different clones) qualitative assessment of the association and dissociation kinetics SELECTION CRITERIA: strongest possible binding to LamP1 binding of laminin from placenta extract exclusion of IgM (in 2 cases) clones having th highest synthetic capacity simultaneous binding to the antigen together with other monoclonal antibodies | 11 pos. clones |
| 4th Selection Reaction with serum | Detection of the high molecular weight serum form (RIA) High affinity for "Serum antigen"? (RIA) First steps in the development of an assay (Table 5) | 5 pos. clones |
| 5th Selection Third biochem. characterization | Electrophoresis, Western Blot and immune staining Determination of binding constants using BIAcore Elaboration of conditions for purifying monoclonal antibodies | 3 pos. clones |

TABLE 5

First steps in assay development

| Recognition of the serum antigen | | experiments |
|---|---|---|
| using a coated-tube method based on the polyclonal antiserum from the RIA-gnost ® LamP1 test. The 5 monoclonal antibodies selected (4th selection) were employed as iodinated second antibodies | Production and purification of the monoclonal antibodies on a 1–5 mg scale | different RIA tubes were coated with the selected antibodies (4th selection); iodinated LamP1 was used as the probe for the surface binding. Optimization of the coating buffer and of the blocking conditions |
| Test antigens: purified serum laminin (high molecular weight and low molecular weight forsm); LamP1 standard from the RIA-gnost ® LamP1 test; normal sera Selection criteria for coated-tube assays: recognition of LamP1 standard and serum laminin (high molecular weight), perceptible reaction with normal serum, proportionality of test maintained on dilution | Production of A27/2/1 and A9/2/1 (100 mg scale) | → best candidate for a coating antibody = A27/2/1 B2 Optimazation of the incubation times, incubation intervals, buffers and serum volumes for the 3 coated-tube variants |

Continuation of the test conditions for three coated-tube methods.

Coating antibody = A27/2/1 B2
Second antibody = A9/2/1 B2
 = A33/2/20
 = polyclonal anti-LamP1 IgG TEST MEASUREMENTS using the three coated-tube methods Determination of antigen distribution in normal sera
Determination of normal concentrations
Tests for crossreactivites
Use for different indications Table 6

Characterization of the monoclonal anti-laminin-P1 antibodies

The concentration and subclass were determined using BIAcore.

The values in the "ELISA" column are given as OD at 405 nm.

In the "Blot" columns, −SH means unreduced, +SH means reduced, +++ means very strong reaction, ++ means strong reaction + means perceptible reaction and − means no reaction. Two batches each of laminin P1 (batch 1 and batch 2) and laminin (batch I and batch II) were used for the binding studies in the BIAcore.

The "pairs" column indicates the antibodies or clones which can bind to laminin P1 at the same time as the antibodies specified in column 1.

TABLE 6

Characterization of the monoclonal anti-laminin P1 antibodies

|  |  |  | ELISA |  | Blot |  |
|---|---|---|---|---|---|---|
| Antibody | Conc. µg/mg | Subtype | Lm P1 | Laminin (S) | Laminin −SH | Laminin +SH |
| A 27/1/1 | 10 |  | 1.57 | 1.061 | +++ | − |
| A 27/1/2 | 20.9 |  | 1.224 | 0.942 |  |  |
| A 27/1/7 | 10.1 (5.2) | IgG2a | 1.488 | 1.058 |  |  |
| A 27/1/8 | 12.8 | IgG2a | 1.503 | 1.038 | +++ | ++ |
| A 9/1/7 | 23.6 | IgG2a | 1.544 | 1.147 | +++ | weak |
| A 9/1/12 | 12.1 | IgG2a | 1.289 | 0.906 |  |  |
| A/9/1/4 | 11.3 |  | 1.556 | 1.046 |  |  |
| A 9/1/9 | 31.0 |  | 1.559 | 1.141 |  |  |
| A 24/1/13 | 10.8 | IgG2a | 1.319 | 1.628 | +++ | weak |
| A 24/1/5 | 21.3 |  | 1.266 | 0.922 |  |  |
| A 24/1/23 | 21.5 |  | 1.782 | 0.854 |  |  |
| A 25/1/2 |  | IgG2a:IgG1 | 2.079 | 2.125 | ++ (1:500) | − |
| A 35/1/2 | 12.9 | IgG1 | 0.816 | 0.01 | weak | + |
| A 33/1/3 | 14.1 | IgG1:IgM | 1.004 | 0.122 |  |  |
| A 33/1/1 | ? | IgM | 1.214 | 0.02 | weak | − |
| A 6/1/7 | ? | IgM | 1.386 | 1.517 | ++ | weak |
| A 6/1/8 | ? | IgM:IgG1 | 1.632 | 1.46 |  |  |
| A 16/1/1 | 6.0 | IgG1 | 0.561 | 0.628 | weak | − |
| A 16/1/6 | 8.6 | IgG1 | 0.76 | 0.592 |  |  |
| A 41/1/7 | 9.1 | IgG1 | 0.327 | 0.416 | weak | − |
| A 50/1/4 | 16.3 | IgG1 | 1.289 | − |  |  |
| A 50/1/5 | 16.6 | IgG1 | 1.406 | − | weak |  |
| A 46/1/5 | 18.5 | IgG1 | 0.33 | − |  |  |
| A 46/1/12 | 38.5 | IgG1 | 0.319 | − |  |  |

|  | BIAcore |  |  |  |  |  |
|---|---|---|---|---|---|---|
|  | Lam P1 |  |  | Lamin (H) |  |  |
| Antibody | CH.1.25 µl | CH.2.4 µl | CH.2.25 µl | CH.1 | CH.2 | Pairs |
| A 27/1/1 |  | 191 RU | 584 RU |  |  | A9/1/7; A24/1/13; A25/1/2 |
| A 27/1/2 |  |  | 638 RU |  |  |  |
| A 27/1/7 |  | 231 RU | 613 RU |  |  | A 50/1/4 |
| A 27/1/8 |  |  | 650 RU |  | 291 |  |
| A 9/1/7 |  | 514 RU | 1050 RU |  | 332 | A27/1/7; A25/1/2; A50/1/4 |
| A 9/1/12 |  | 418 RU | 774 |  | 300 |  |
| A/9/1/4 |  |  | 794 |  | 309 |  |
| A 9/19 |  |  | (1:3) 661 |  | 323 |  |
| A 24/1/13 | 833 RU | 345 RU | 737 RU | + |  | A33/1; A27/1/7; A25/1/2 |
| A 24/1/5 |  |  |  |  | 280 | A50/1/5; A33/1/1; A50/1/4 |
| A 24/1/23 |  |  |  |  | 276 |  |
| A 25/1/2 | 410 RU | 443 RU | 331 RU (1:10) | + | − | A24/1/6; A27/1/1; A50/1/4 |
| A 35/1/2 | 148 RU | 48 RU | 129 RU |  |  |  |
| A 33/1/3 |  | 143 RU | 404 RU |  |  |  |
| A 33/1/1 |  | 161 RU |  |  |  |  |
| A 6/1/7 | 622 RU | 272 RU |  | + |  |  |
| A 6/1/8 | 640 RU | 275 RU | 495 RU |  |  |  |
| A 16/1/1 |  | 26 RU | 77 RU |  |  |  |
| A 16/1/6 |  | 35 RU | 103 RU |  |  |  |
| A 41/1/7 |  | 6 RU |  |  |  |  |
| A 50/1/4 |  | 681 RU | 947 RU |  | − | A9/1/7; A24/1/13; A27/1/8 |
| A 50/1/5 | 261 RU | 157 RU | 185 RU |  | − | A24/1/13; A28/1/1 |
| A 46/1/5 |  | 241 RU | 372 RU |  |  |  |
| A 46/1/12 |  | 380 RU | 576 RU |  | − | A9/1/7; A24/2/2; A27/1/8 (A25/1/2) |

TABLE 7

Final criteria for deciding to select clones for developing a test

| Coating | Sandwich using poly K4 (1/93) |  |  |  | Lam batch I ug/ml | Serum P1 ug/ml | Serum P2 ug/ml | Human serum | cpm |
|---|---|---|---|---|---|---|---|---|---|
|  | Di1/µg/ml | Standard ng/ml | cpm | % bind |  |  |  |  |  |
| 28/1/1 v. 7.6.91 | 1:20 | 49 | S0 | 70 | 10.6 | 14 | 1.7 | 200 ul 300/90 | 699 |

TABLE 7-continued

Final criteria for deciding to select clones for developing a test

| Coating | Sandwich using poly K4 (1/93) | | | | | Lam batch I ug/ml | Serum P1 ug/ml | Serum P2 ug/ml | Human serum | cpm |
|---|---|---|---|---|---|---|---|---|---|---|
| | Dil/µg/ml | | Standard ng/ml | | % bind | | | | | |
| | | | S1 | 35.6 | 5632 | | | | test serum | 1217 |
| | | | S4 | 284 | 29721 | | | | 52/89 | 843 |
| | | | S7 | 2400 | 79393 | 51 | | | | |
| | | | | | | | | | 200 ul | |
| 24/2/2 (075) | 1:10 | 12.6 | S0 | | 116 | 5.7 | 9.6 | 1.6 | 300/90 | 145 |
| | | | S1 | 35.6 | 4073 | 3 | | | test serum | 489 |
| | | | S4 | 284 | 22989 | 16 | | | 52/89 | 172 |
| | | | S7 | 2400 | 58777 | 42 | | | | |
| | | | | | | | | | 200 ul | |
| 27/2/1 (071) | 1:10 | 190 | S0 | | 167 | 19.8 | 9.9 | 1.6 | 300/90 | 11621 |
| | | | S1 | 35.6 | 5155 | | | | test serum | 19554 |
| | | | S4 | 284 | 30580 | | | | 52/89 | 15602 |
| | | | S7 | 2400 | 71761 | 46 | | | | |
| | 1:30 | 65 | S0 | | 193 | | | | 300/90 | 11117 |
| | | | | | | | | | (100 ul) | |
| | | | S1 | 35.6 | 5623 | | | | | |
| | | | S4 | 284 | 29596 | | | | | |
| | | | S7 | 2400 | 66547 | 47 | | | | |
| | | | | | | | | | 200 ul | |
| 27/2/1 (074) | 1:10 | 26 | S0 | | 66 | 19.3 | 9.4 | 1.7 | 300/90 | 9234 |
| | | | S1 | 35.6 | 4931 | 3 | | | test serum | 13258 |
| | | | S4 | 284 | 25524 | 18 | | | 52/89 | 13843 |
| | | | S7 | 2400 | 63453 | 45 | | | | |
| | | | | | | | | | 200 ul | |
| 9/2/1 (072) | 1:10 | 10 | S0 | | 91 | 12.7 | 11 | 1.3 | 300/90 | 1480 |
| | | | S1 | 35.6 | 5198 | 3.6 | | | | 2995 |
| | | | S4 | 284 | 28286 | 20 | | | | 1999 |
| | | | S7 | 2400 | 63388 | 45 | | | | |

"Standard cpm or % binding" Comparison of recognition of RIAgnost standard
"Lam batch I" Binding to laminin which was purified as described under methods
"Serum P1 and Serum P2" High molecular weight and low molecular weight serum antigen, respectively; purified from ≈ 20 ml of normal human serum
"Human serum" Binding of the antigen in human test sera. Clones A28/1/1 and A24/2/2 are unsuitable for this owing to their unsatisfactory reaction.

TABLE 8

Crossreactions

| Tracer Antigen | Test concentration E/ml (µg/ml) | A9/2/1B2 | | | A33/2/20 | | |
|---|---|---|---|---|---|---|---|
| | | counts | % binding | calculated concentration | counts | % binding | calculated concentration |
| LamP1 | 0 | 289 | 0.18 | | 102 | 0.09 | |
| Standard | 0.17 (0.037) | 4140 | 2.6 | | 1606 | 1.41 | |
| | 1.43 (0.31) | 32050 | 20.2 | | 13066 | 11.5 | |
| | 12 (2.64) | 142523 | 89.9 | | 51264 | 45 | |
| Collagen I (Chemicon) | 5 | 607 | 0.38 | | 807 | 0.71 | |
| | 1 | 340 | 0.21 | | 287 | 0.25 | |
| Collagen III (Chemicon) | 5 | 331 | 0.21 | | 138 | 0.12 | |
| | 1 | 316 | 0.2 | | 114 | 0.1 | |
| Collagen IV (Chemicon) | 5 | 527 | 0.33 | | 120 | 0.11 | |
| | 1 | 333 | 0.21 | | 114 | 0.1 | |
| Collagen V (Chemicon) | 5 | 614 | 0.39 | | 241 | 0.21 | |
| | 1 | 455 | 0.29 | | 232 | 0.2 | |
| Collagen VI (Chemicon) | 6.6 | 378 | 0.24 | | 262 | 0.23 | |
| | 1.32 | 533 | 0.34 | | 161 | 0.14 | |
| Fibronectin (Chemicon) | 5 | 413 | 0.26 | | 141 | 0.12 | |
| | 1 | 463 | 0.29 | | 148 | 0.13 | |
| Fibrinogen (Sigma) | 5 | 367 | 0.23 | | 171 | 0.15 | |
| | 1 | 279 | 0.18 | | 151 | 0.13 | |
| Coll. VI a3Nt Dr. Timp1 | 3.3 | 349 | 0.22 | | 148 | 0.13 | |
| | 0.66 | 381 | 0.24 | | 130 | 0.11 | |
| NC 1 own isolate | 5 | 330 | 0.21 | | 122 | 0.11 | |
| | 1 | 407 | 0.26 | | 174 | 0.15 | |
| 7S (DE10) own isolate | 5 | 303 | 0.19 | | 159 | 0.14 | |
| | 1 | 311 | 0.2 | | 132 | 0.12 | |
| 7S (DE6) | 5 | 271 | 0.17 | | 160 | 0.14 | |

TABLE 8-continued

| | | Crossreactions | | | | | |
|---|---|---|---|---|---|---|---|
| | Test | A9/2/1B2 | | | A33/2/20 | | |
| Tracer Antigen | concentration E/ml (µg/ml) | counts | % binding | calculated concentration | counts | % binding | calculated concentration |
| own isolate | 1 | 336 | 0.21 | | 230 | 0.2 | |
| EHS-LN | 7 | 279 | 0.18 | | 186 | 0.16 | |
| Dr. Timp1 | 1.4 | 306 | 0.19 | | 250 | 0.22 | |
| EHS-LamP1 | 6.8 | 466 | 0.29 | | 270 | 0.24 | |
| Dr. Timp1 | 1.36 | 381 | 0.24 | | 282 | 0.25 | |
| Laminin | 6.73 | 18210 | 11.5 | 0.176 µg/ml | 4009 | 3.52 | 0.095 µg/ml |
| (Chemicon) | 1.35 | 4290 | 2.7 | 0.039 µg/ml | 974 | 0.86 | |
| Merosin | 5 | 127867 | 80.7 | 2.05 µg/ml | 25468 | 22.3 | 0.68 µg/ml |
| (Chemicon) | 1 | 35812 | 22.6 | 0.36 µg/ml | 5632 | 4.9 | 0.13 µg/ml |

TABLE 9

Normal values:

| | n | Average value E/ml | Median E/ml |
|---|---|---|---|
| RIA-gnost ® Lam-P1 | 126 | 1.32 ± 0.18 | 1.31 |
| A27/2/1-A9/2/1 | 23 | 0.864 ± 0.212 | 0.849 |
| A27/2/1-A33/2/20 | 24 | 0.073 ± 0.038 | 0.065 |

TABLE 10

Primary biliary cirrhosis

| | n | Average value E/ml | Median E/ml | Increase as compared with the normal value | Correlation with RIA-gnost ® $r^2$ |
|---|---|---|---|---|---|
| RIA-gnost ® Lam-P1 | 42 | 2.28 ± 0.57 | 2.41 | 1.72 | |
| A27/2/1-A9/2/1 | 42 | 1.98 ± 0.96 | 2.03 | 2.29 | 0.49 |
| A27/2/1-A33/2/20 | 42 | 0.45 ± 0.4 | 0.34 | 6.16 | 0.28 |

TABLE 11

Alcoholic toxic liver cirrhosis

| | n | Average value E/ml | Median E/ml | Increase as compared with the normal value | Correlation with RIA-gnost ® $r^2$ |
|---|---|---|---|---|---|
| RIA-gnost ® Lam-P1 | 58 | 3.14 ± 0.98 | 3.15 | 2.38 | |
| A27/2/1-A9/2/1 | 58 | 3.71 ± 2.08 | 3.19 | 4.29 | 0.69 |
| A27/2/1-A33/2/20 | 58 | 0.9 ± 0.59 | 0.69 | 12.3 | 0.21 |

TABLE 12

Chronically active heptatitis

| | n | Average value E/ml | Median E/ml | Increase as compared with the normal value | Correlation with RIA-gnost ® $r^2$ |
|---|---|---|---|---|---|
| RIA-gnost ® Lam-P1 | 26 | 2.20 ± 0.58 | 2.45 | 1.7 | |
| A27/2/1-A9/2/1 | 26 | 2.35 ± 1.09 | 2.16 | 2.7 | 0.26 |
| A27/2/1-A33/2/20 | 22 | 0.53 ± 0.45 | 0.38 | 7.3 | 0.05 |

TABLE 13

Decompensated liver cirrhosis

| | n | Average value E/ml | Median E/ml | Increase as compared with the normal value | Correlation with RIA-gnost ® $r^2$ |
|---|---|---|---|---|---|
| RIA-gnost ® Lam-P1 | 23 | 2.71 ± 1.29 | 2.26 | 2.05 | |
| A27/2/1-A9/2/1 | 19 | 3.05 ± 1.77 | 2.84 | 3.53 | 0.93 |
| A27/2/1-A33/2/20 | 19 | 0.664 ± 0.556 | 0.38 | 9.14 | 0.41 |

TABLE 14

Liver cirrhosis of unidentified origin

| | n | Average value E/ml | Median E/ml | Increase as compared with the normal value | Correlation with RIA-gnost ® $r^2$ |
|---|---|---|---|---|---|
| RIA-gnost ® Lam-P1 | 15 | 3.25 ± 1.03 | 3.18 | 2.46 | |
| A27/2/1-A9/2/1 | 14 | 4.52 ± 1.99 | 4.48 | 5.23 | 0.43 |
| A27/2/1-A33/2/20 | 14 | 1.09 ± 0.56 | 1.14 | 14.9 | 0.8 |

TABLE 15

Posthepatic liver cirrhosis

|  | n | Average value E/ml | Median E/ml | Increase as compared with the normal value | Correlation with RIA-gnost® $r^2$ |
|---|---|---|---|---|---|
| RIA-gnost® Lam-P1 | 26 | 2.96 ± 1.03 | 2.93 | 2.24 |  |
| A27/2/1-A9/2/1 | 25 | 2.82 ± 1.3 | 2.29 | 3.26 | 0.35 |
| A27/2/1-A33/2/20 | 25 | 0.583 ± 0.452 | 0.45 | 7.99 | 0.28 |

TABLE 16

Cancers

A. Serum from a patient suffering from hepatocellular carcinoma

|  | RIA-gnost® Lam-P1 | A27/2/1-A9/2/1 | A27/2/1-A33/2/20 |
|---|---|---|---|
| Laminin E/ml | 3.4 | 3.6 | 0.45 |
| Increase | 2.6 | 4.2 | 6.2 |

B. Patients suffering from lung cancer

| Patient | RIA-gnost® Lam-P1 E/ml | A27/2/1-A9/2/1 E/ml | A27/2/1-A33/2/20 E/ml |
|---|---|---|---|
| MC | 3.01 | 1.81 | 0.183 |
| JV | 2.7 | 1.25 | 0.054 |
| EU | 2.8 | 2.4 | 0.200 |

TABLE 17

Diabetes

|  | n | Average value E/ml | Median E/ml | Deviation as compared with the normal value | Correlation with RIA-gnost® $r^2$ |
|---|---|---|---|---|---|
| RIA-gnost® Lam-P1 | 78 | 1.70 ± 0.30 | 1.66 | 1.3 |  |
| A27/2/1-A9/2/1 | 80 | 0.73 ± 0.37 | 0.58 | 0.84 | 0.61 |
| A27/2/1-A33/2/20 | 80 | 0.057 ± 0.064 | 0.039 | 0.53 | 0.05 |

The study involved the investigation of the sera from 80 hospitalized diabetics (32% type I and 68% Type II) who had a diabetes history of 11–14 years (Stracke, H.; Wiek, K.; Günzler, V.; Federlin, K. (1993) Die Medizinische Welt 44; 383 to 385) and in whom cheiropathy (36%), retinopathy (48%), neuropathy (66%), and nephropathy (39%) were diagnosed.

BRIEF DESCRIPTION OF THE DRAWINGS

FIG. 1(b): The domain structure of the amino-terminal arms of laminin showing the P1 region.

Figure 1A:
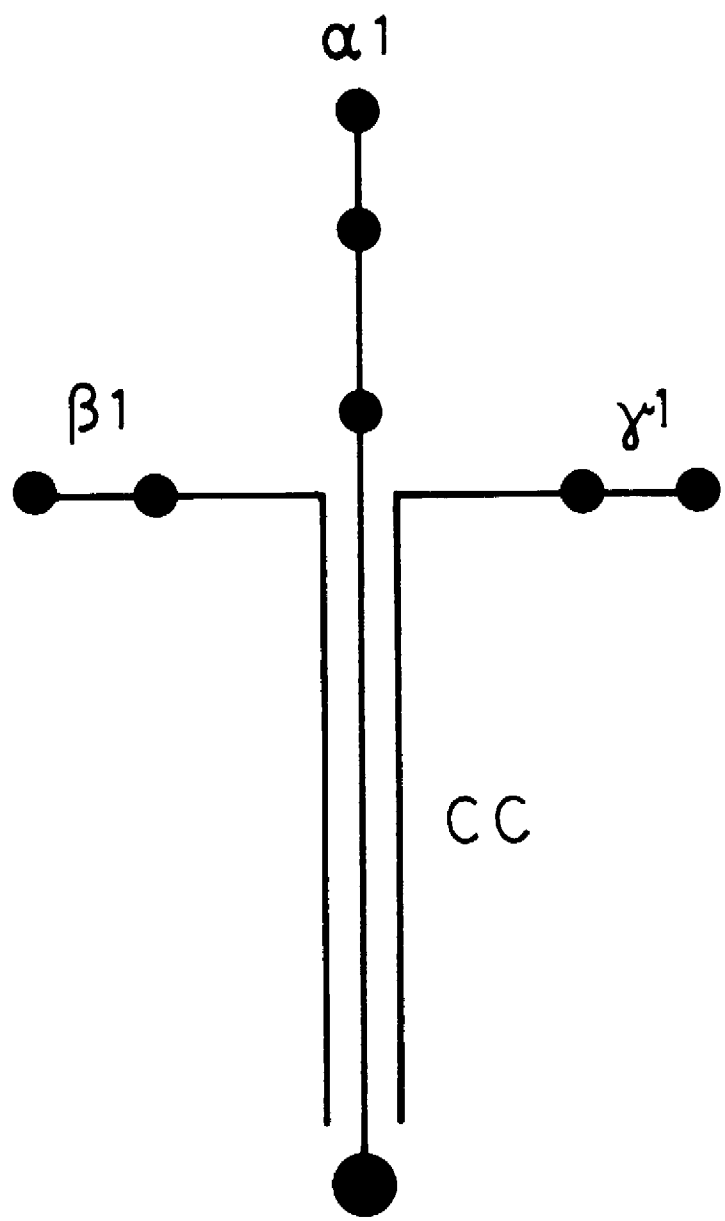
FIG. 1(a): The structure of laminin showing the α, β, and γ polypeptide chains.
Figure 2:
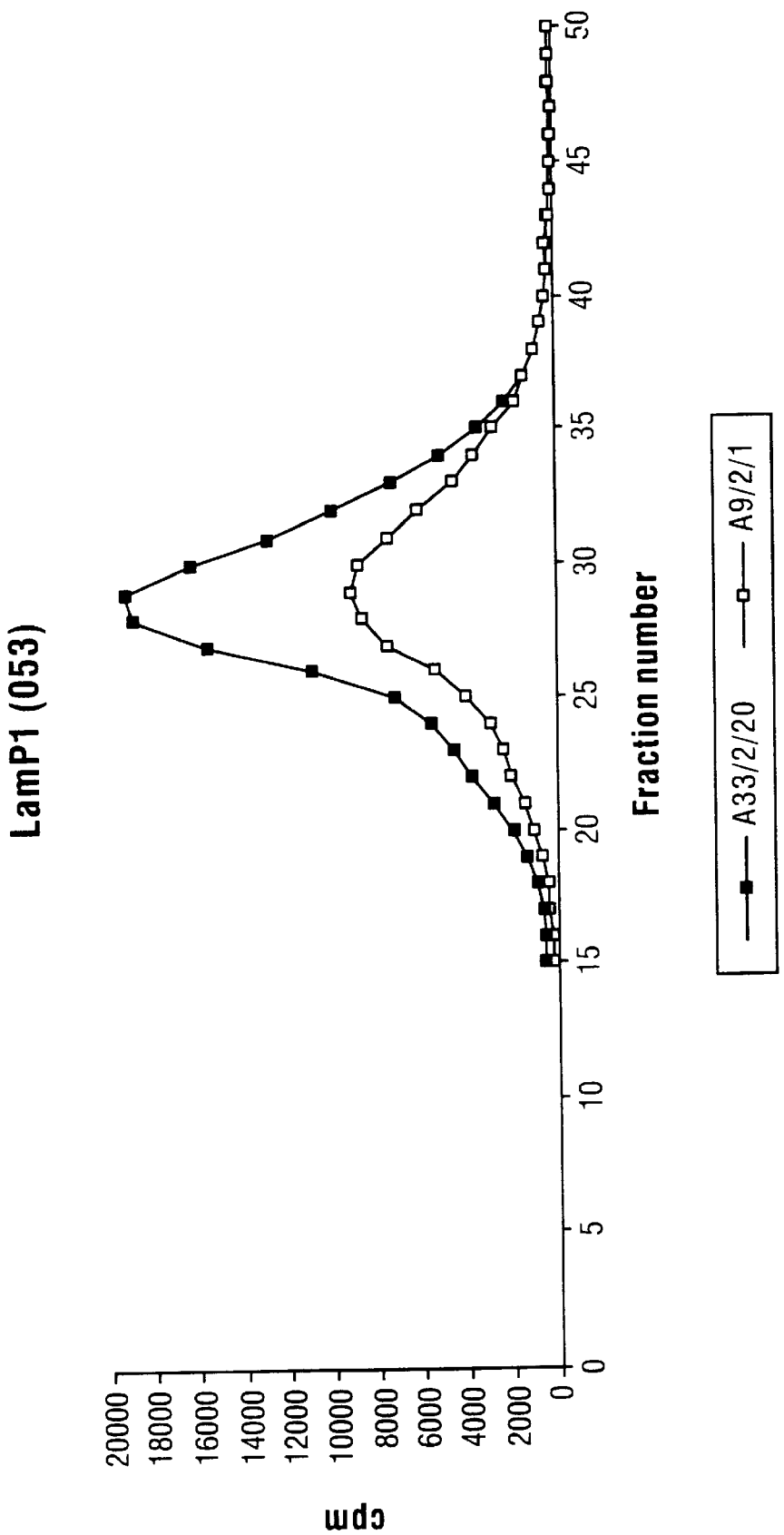
FIG. 2: Size distribution of anti-A33/2/20 and anti-A9/2/1 antigenicity against laminin P1 fractionated by molecular weight on a Sepharose S-400 column.
Figure 3:
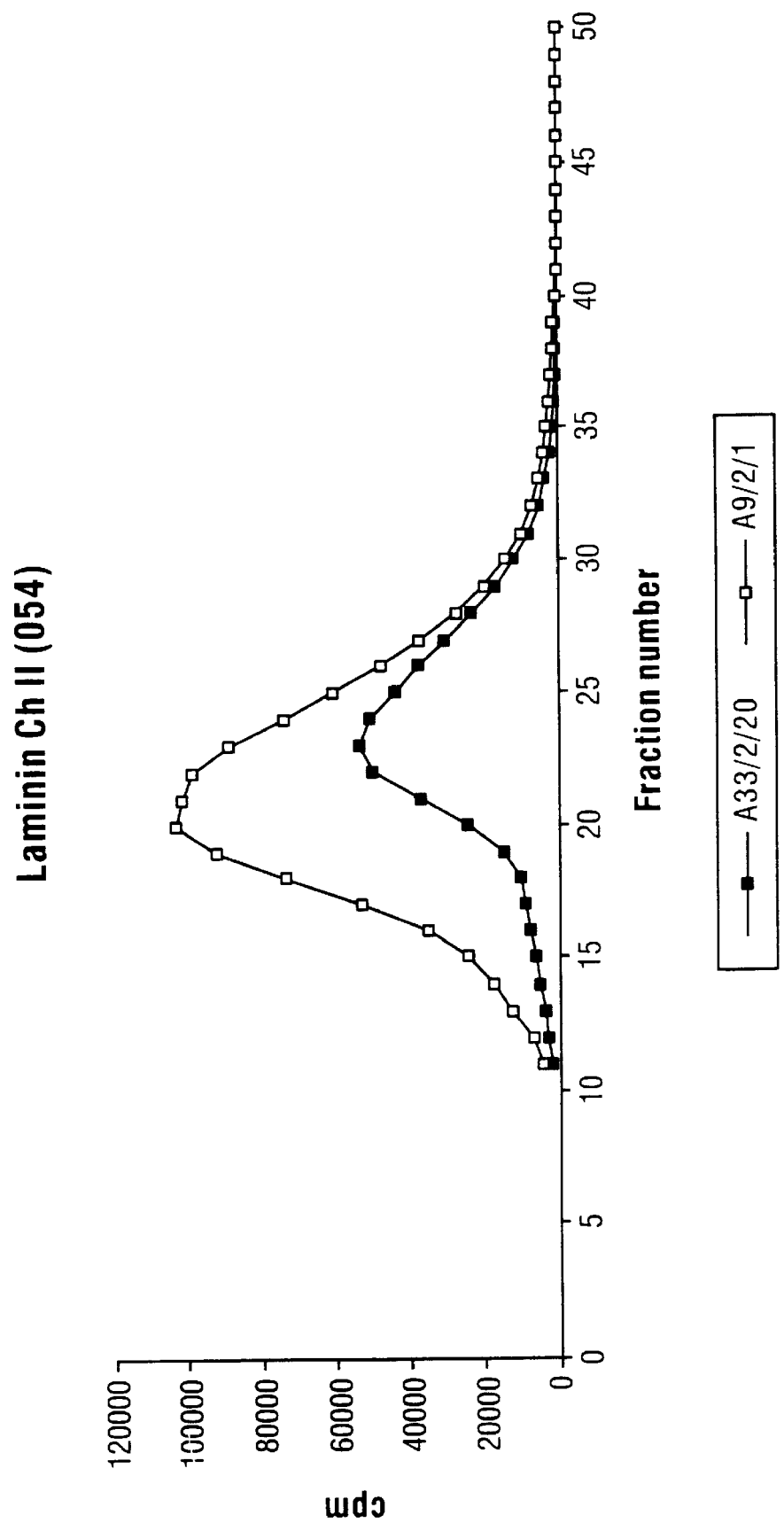
FIG. 3: Size distribution of anti-A33/2/20 and anti-A9/211 antigenicity against human laminin (batch II) fractionated by molecular weight on a Sepharose S-400 column.
Figure 4:
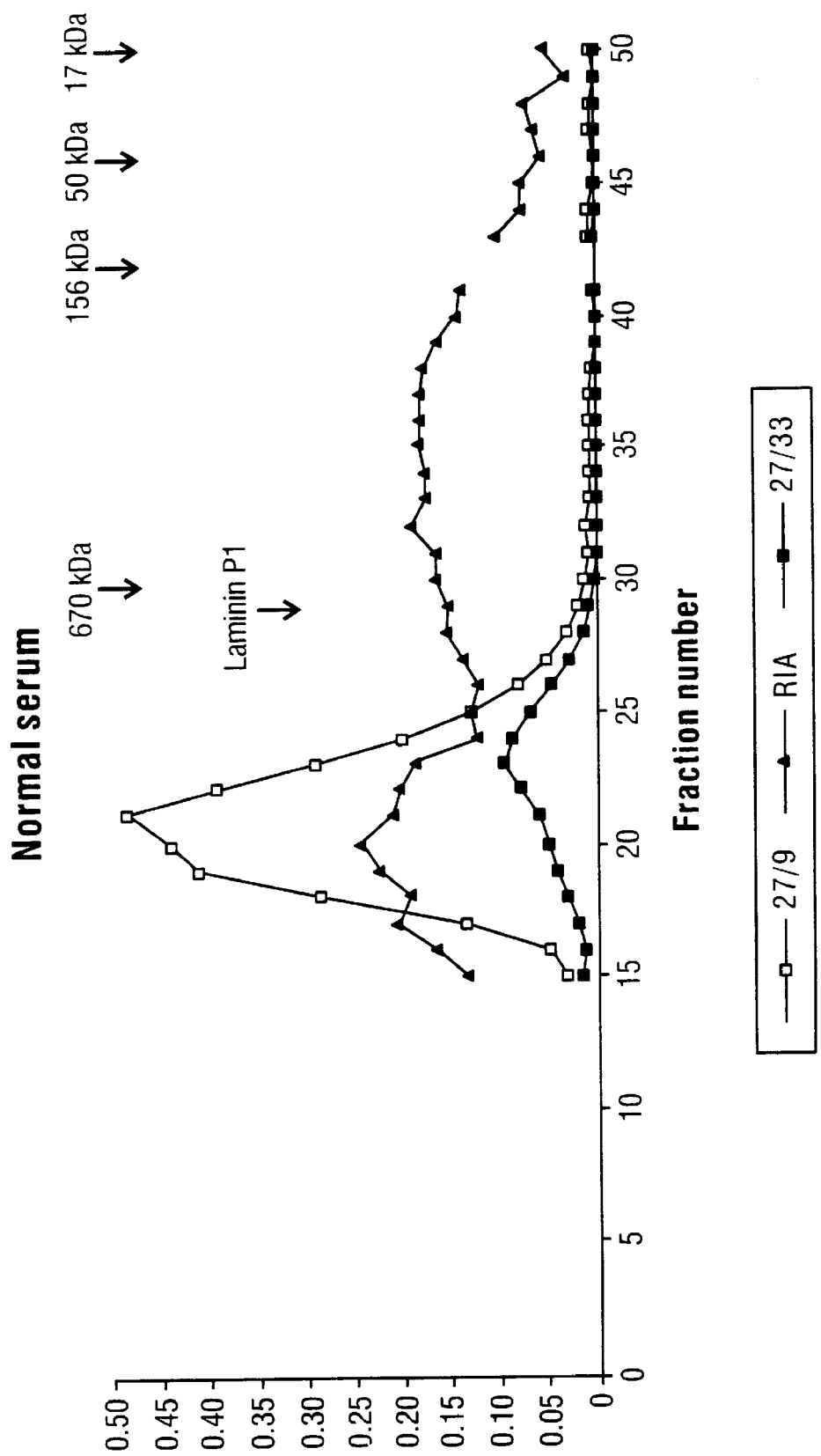
FIG. 4: Size distribution of anti-A33/2/20, anti-A9/2/, and anti RIA-gnost® antigenicity against normal human serum fractionated by molecular weight on a Sepharose S-400 column.
Figure 5:
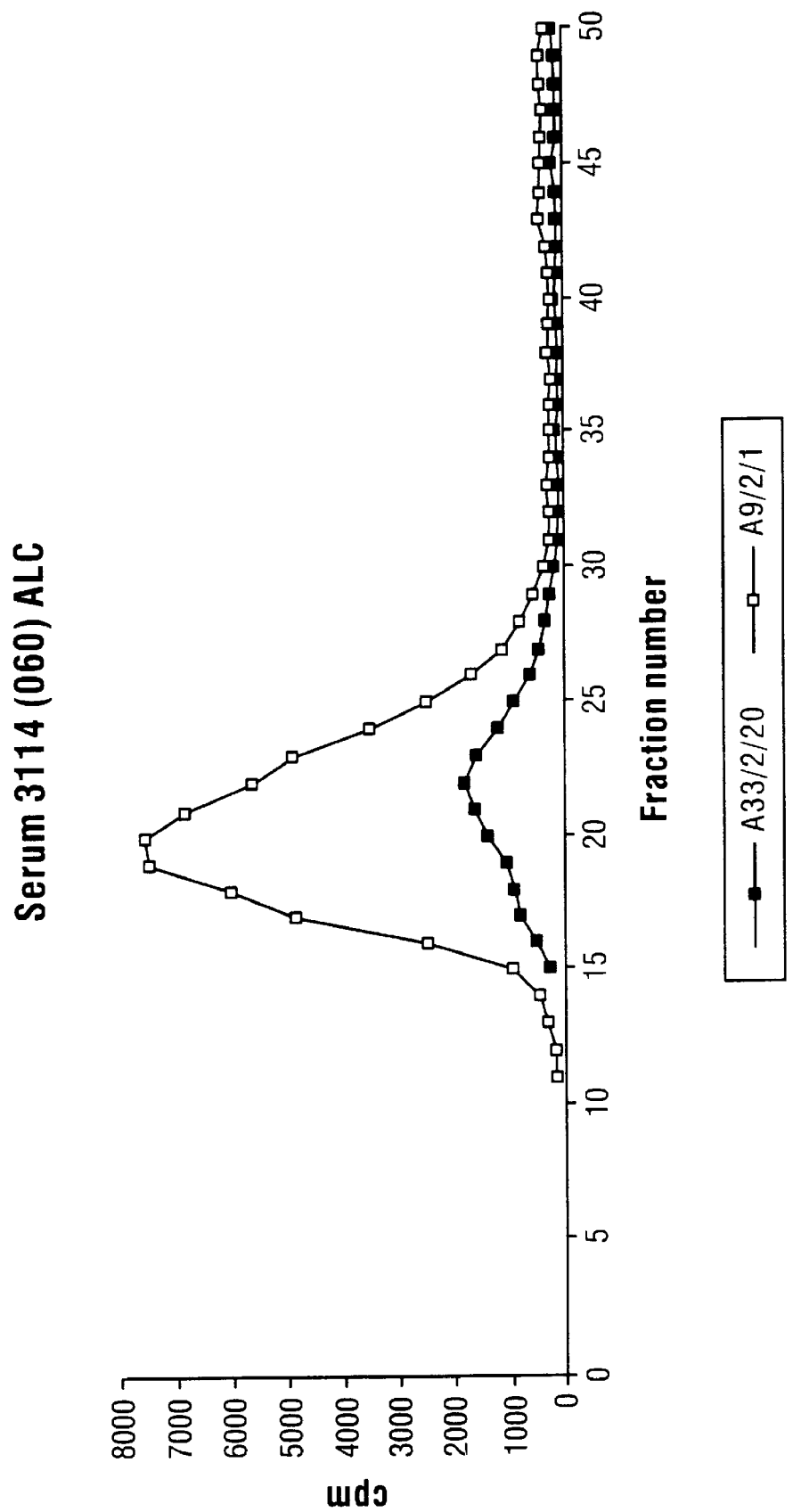
FIG. 5: Size distribution of anti-A33/2/20 and anti-A9/2/1 antigenicity against human serum from a patient suffering from alcoholic liver disease (ALC) fractionated by molecular weight on a Sepharose S-400 column.
Figure 6:
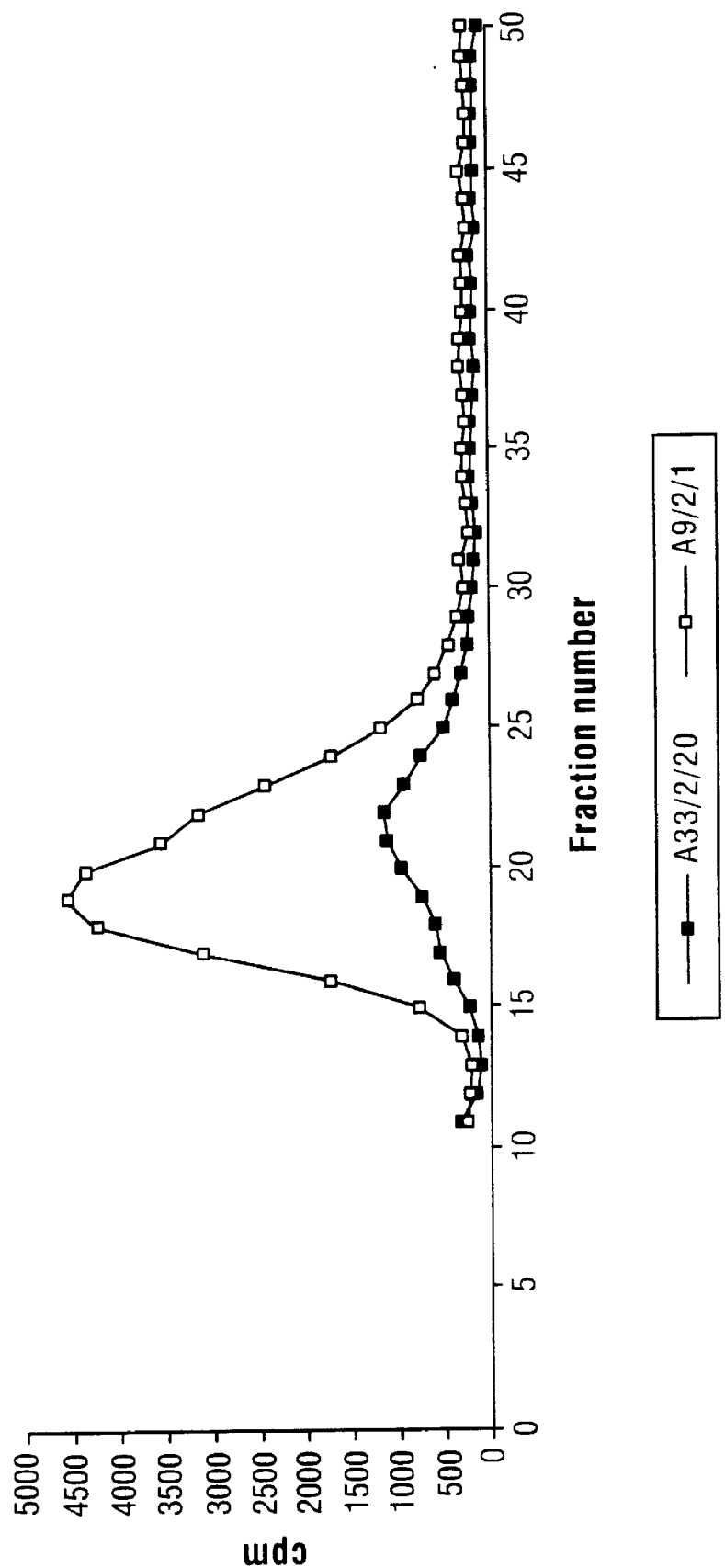
FIG. 6: Size distribution of anti-A3312/20 and anti-A91/21 antigenicity against human serum from a patient suffering from PBC fractionated by molecular weight on a Sepharose S-400 column.
Figure 7:
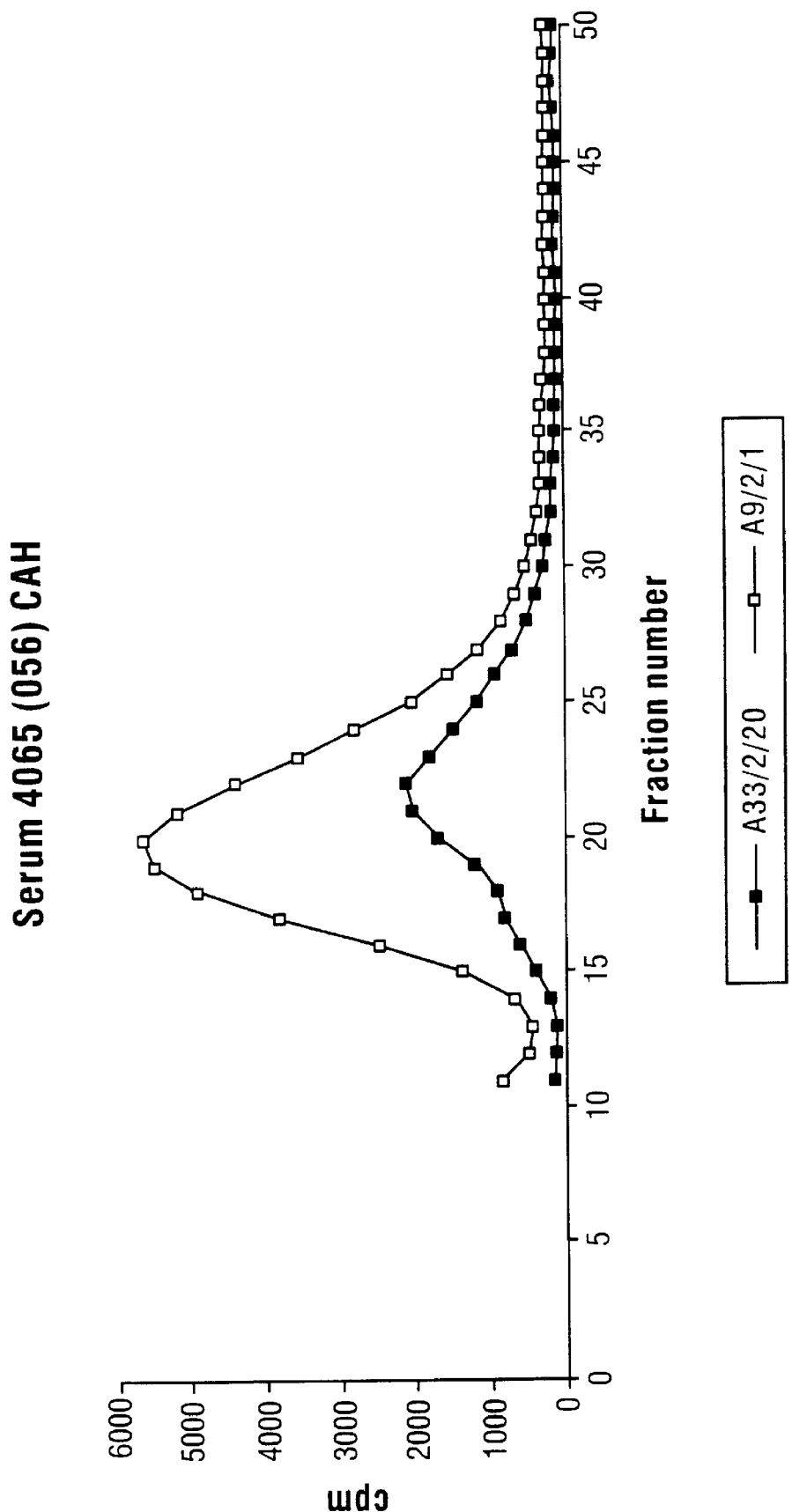
FIG. 7: Size distribution of anti-A33/2/20 and anti-A9/2/1 antigenicity against human serum from a patient suffering from CAH fractionated by molecular weight on a Sepharose S-400 column
Figure 8:
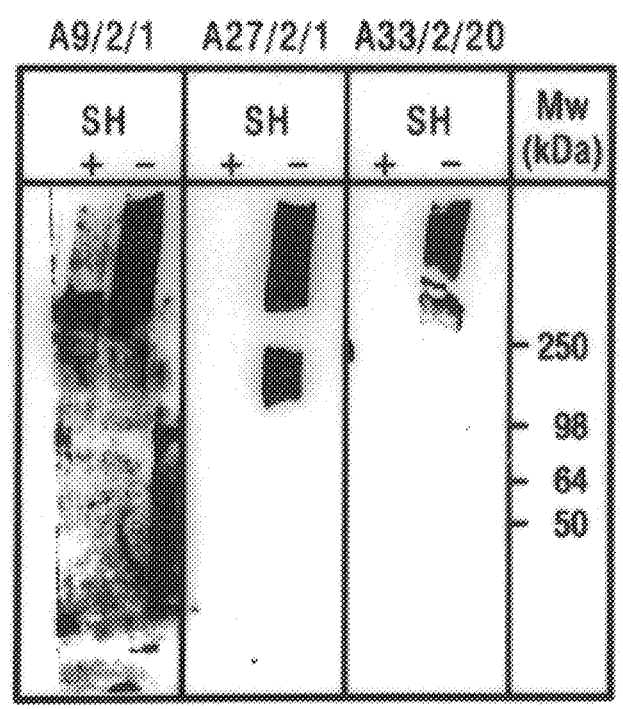
FIG. 8: Semi-dry blot attained by the standard protocol using a discontinuous buffer system after separating approximately 1 μg of laminin batch II by SDS gel electrophoreses under reducing and non-reducing conditions and probed with antibodies A9/2/1, A271211 or A33/2/20.

We claim:

1. A monoclonal antibody that binds intact high molecular weight laminin in human serum, and recognizes structural motifs of the laminin P1 domain which are folded in the native manner, but does not specifically bind to laminin degradation products in body fluids which do not contain structural motif of the laminin P1 domain folded in the native manner.

2. A monoclonal antibody as claimed in claim 1, wherein the antibody is formed by a hybridoma which arose by fusing cells from a myeloma cell line and lymphocytes from a vertebrate, which had previously been immunized with Laminin P1.

3. A monoclonal antibody as claimed in claim 1 which shows no measurable dissociation from a human laminin affinity matrix.

4. Two monoclonal antibodies as claimed in claim 1, which have the ability to bind to the antigen as a pair.

5. A monoclonal antibody as claimed in claim 1, which is assigned to the IgG 2a subclass.

6. A monoclonal antibody as claimed in claim 1, which is assigned to the IgG 1 subclass.

7. A monoclonal antibody as claimed in claim 5, which is produced by the hybridoma cell line DSM ACC2181.

8. A monoclonal antibody as claimed in claim 5, which is produced by the hybridoma cell line DSM ACC2180.

9. A monoclonal antibody as claimed in claim 6, which is produced by the hybridoma cell line DSM ACC2182.

10. A hybridoma cell line which produces an antibody as claimed in claim 1 and which can be prepared by fusing cells from a myeloma cell line and lymphocytes from a vertebrate, which has previously been immunized with laminin P1, and subsequently selecting the hybrids on the basis of whether the antibody produced by the hybrid also exhibits, in addition to good binding affinity for purified human laminin from placenta, a good reaction with the high molecular weight form of the laminin isolated from human serum and, wherein the antibody specifically binds intact high molecular weight laminin in human serum, but does not specfically bind to laminin degradation products in body fluids which do not contain structural motifs of the laminin P1 domain folded in the native manner.

11. A hybridoma cell line as claimed in claim 10 wherein the lymphocytes are removed from mice of the Balb/c strain which have been immunized with laminin P1 and the myeloma cell line is the mouse myeloma cell line P3X63AG8.653.

12. The hybridoma cell line DSM ACC2181.
13. The hybridoma cell line DSM ACC2180.
14. The hybridoma cell line DSM ACC2182.
15. A process for preparing a monoclonal antibody as claimed in claim 1, wherein
  a) vertebrates are immunized with the laminin P1 fragment which can be prepared from human placenta by pepsin digestion,
  b) lymphocytes are isolated from the immunized vertebrates and fused with myeloma cells,
  c) the hybrids are selected for the presence of an antibody having specificity for proteins from the family of the laminins and the laminin P1 fragment which can be prepared from human placenta by pepsin digestion, wherein the monoclonal antibody specifically binds to the structures of the laminin P1 domain of laminin which are folded in the native manner and the affinity of the antibody for intact, native laminin is approximately equal to the affinity of the antibody for the laminin P1 fragment, wherein the antibody specifically binds intact high molecular weight laminin in human serum, but does not specially bind to laminin degradation products in body fluids which do not contain structural motifs of the laminin P1 domain folded in the native manner, and is cloned, and
  d) the antibody is isolated from these clones.
16. The process as claimed in claim 15, wherein the hybridoma cell lines DSM ACC2181, DSM ACC2180 or DSM ACC2182 are employed for carrying out process step d) in claim 15.
17. A hybridoma cell line which produces an antibody as claimed in claim 1.

* * * * *